US012605390B2

(12) United States Patent
Faltum et al.

(10) Patent No.: US 12,605,390 B2
(45) Date of Patent: Apr. 21, 2026

(54) TREATMENT OF CANCER AND INHIBITION OF METASTASIS

(71) Applicant: Celex Oncology Innovations Limited, London (GB)

(72) Inventors: Carsten Faltum, Vitznau (CH); Leif Helth Jensen, Vitznau (CH); Mustafa Djamgoz, London (GB)

(73) Assignee: Celex Oncology Innovations Limited, London (GB)

( * ) Notice: Subject to any disclaimer, the term of this patent is extended or adjusted under 35 U.S.C. 154(b) by 1023 days.

(21) Appl. No.: 17/512,326

(22) Filed: Oct. 27, 2021

(65) Prior Publication Data

US 2022/0125800 A1 Apr. 28, 2022

Related U.S. Application Data

(63) Continuation of application No. 16/484,997, filed as application No. PCT/EP2018/053457 on Feb. 12, 2018, now abandoned.

(30) Foreign Application Priority Data

Feb. 10, 2017 (DK) ................................ 2017 70091

(51) Int. Cl.
*A61K 31/553* (2006.01)
*A61P 35/04* (2006.01)

(52) U.S. Cl.
CPC ............ *A61K 31/553* (2013.01); *A61P 35/04* (2018.01)

(58) Field of Classification Search
CPC .............................. A61K 31/553; A61K 35/04
See application file for complete search history.

(56) References Cited

U.S. PATENT DOCUMENTS

2012/0245144 A1 9/2012 Heffron et al.
2015/0283149 A1 10/2015 Belardinelli et al.
2017/0007617 A1 1/2017 Strickley

FOREIGN PATENT DOCUMENTS

EP 2 394 646 12/2011
WO WO 2012/049439 A1 4/2012
WO WO 2012/049440 A1 4/2012
WO WO 2015/017661 A1 2/2015

OTHER PUBLICATIONS

Gao, R.; Shen, Y.; Cai, J.; et al. "Expression of voltage-gated sodium channel a subunit in human ovarian cancer" Oncology Reports 23: 1293-1299, 2010. (Year: 2010).*

(Continued)

*Primary Examiner* — Andrew D Kosar
*Assistant Examiner* — John D McAnany
(74) *Attorney, Agent, or Firm* — Womble Bond Dickinson (US) LLP

(57) ABSTRACT

Compounds and methods are disclosed for reducing or preventing metastatic behaviour in VGSC expressing cancer by the effect of at least reducing the persistent part of the voltage gated sodium channel current without eliminating the transient part, thereby inhibiting the metastatic and invasive growth of malignant cells in a cancer patient.

21 Claims, 12 Drawing Sheets

(56) References Cited

OTHER PUBLICATIONS

Guo, G., et al., "Voltage-gated sodium channels and tumor," Shenyang Pharmaceutical University, 2013, vol. 30(9), pp. 733-739.
Abdul, M. et anon., "Voltage-Gated Sodium Ion Channels in Prostate Cancer: Expression and Activity," *Antican Research,* 2002, vol. 22(3), pp. 1727-1730.
Brackenbury, William J., "Voltage-gated sodium channels and metastatic disease," *Channels,* 2012 vol. 6(5), pp. 352-361.
Clinical Trials Gov. Identifier: NCT02104583, "Evaluating Ventricular Arrhythmia in Subjects With Implantable Cardioverter Defibrillator or Cardiac Resynchronization Therapy-Defibrillator (TEMPO)," Gilead Sciences, 2014, pp. 1-10.
Clinical Trials Gov. Identifier NCT02291237, "Effect of Eleclazine (GS-6615) on Exercise Capacity in Subjects With Symptomatic Hypertrophic Cardiomyopathy (LIBERTY-HCM)," Gilead Sciences, 2014, pp. 1-7.
Diss, J., et al., "Expression Profiles of Voltage-Gated Na+ Channel α-Subunit Genes in Rat and Human Prostate Cancer Cell Lines," *The Prostate,* 2001, vol. 48(3), pp. 165-178.
Djamgoz, Mustafa B. A., Chapter 12, Bioelectricity of Cancer,Voltage-Gated Ion Channels and Direct Current Electric Fields, *The Physiology of Bioelectricity in Development, Tissue Regeneration and Cancer,* 2011, (Ed: Pullar CE), CRC Press, Boca Raton, Florida.
"End of the Road for Eleclazine and Liberty HCM Study: Eleclazine: The Liberty HCM Trial," 2016, *HCM Beat*, pp. 1/3-3/3.
Fairhurst, C., et al., "Sodium channel-inhibiting drugs and survival of breast, colon and prostate cancer: a population-based study,," *Scientific Reports,* 2015, vol. 5(16758), pp. 1-9.
Fraser,S., et al. , "Voltage-Gated Sodium Channel Expression and Potentiation of Human Breast Cancer Metastasis," *Clin Cancer Res,* 2005, vol. 11(15), pp. 5381-5389.
Fuller, H., et al., "Eleclazine, a new selective cardiac late sodium current inhibitor, confers concurrent against autonomically induced atrial premature beats, repolarization alternans and heterogeneity, and atrial fibrillation in an intact porcine model," *Heart Rhythm,* 2016, vol. 13(8), pp. 1679-1686.
Grimes, J., et al., "Differential expression of voltage—activated $Na^+$ currents in two prostatic tumour cell lines: contribution to invasiveness in vitro," *FEBS Letters,* 1995, vol. 369, pp. 290-294.
Martin, F., et al., "Therapeutic Value of Voltage-Gated Sodium Channel Inhibitors in Breast, Colorectal, Prostate Cancer: A systematic Review," *Frontiers in Pharmacology,* 2015, vol. 6 (Article 273), pp. 1-11.
Moss, A., et al., "Ranolazine Shortens Repolarization in Patients with Sustained Inward Sodium Current Due to Type-3 Long QT Syndrome," *J. Cardiovasc Electrophysiol,* 2008, vol. 19(12), pp. 1289-1293.
Onkal, R., et al., "Alternative Splicing of Nav1.5: An Electrophysiological Comparison of 'Neonatal' and 'Adult' Isoforms and Critical Involvement of a Lyusine Residue," *Journal of Cellular Physiology,* 2008, vol. 216, pp. 716-726.
Palmer, C., et al., "Single cell adhesion measuring apparatus (SCAMA): application to cancer cell lines of different metastatic potential and votage-gated $Na^+$ channel expression," *Eur Biophys J.,* 2008, vol. 37, pp. 259-368.
Rajamani, S., et al., "The novel late Na+ current inhibitor, GS-6615 (eleclazine) and its anti-arrhythmic effects in rabbit isolated preparations," *British Journal of Pharmacology,* 2016, vol. 173(21), pp. 3088-3098.
Roger, S., et al., Voltage-gated sodium channels and cancer: is excitability their primary role?, *Frontiers in Pharmacology,* 2015, vol. 6 (Article 152), pp. 1-22.
Trendowski, Matthew, "The inherent metastasis of leukemia and its exploitation by sonodynamic therapy," *Critical Reviews in Oncology/Hematology,* 2015, vol. 94(2), pp. 149-163.
Zablocki, J., et al., "Discovery of Dihydrobenzoxazepinone (GS-6615) Late Sodium Current Inhibitor (Late $I_{NA}$i), a Phase II Agent with Demonstrated Preclinical Anti-Ischemic and Atiarrhythmic Properties," *Journal of Medicinal Chemistry*, 2016, vol. 59, pp. 9005-9017.
Antzelevitch et al. "Electrophysiologic Effects of Ranolazine. A Novel Anti-Anginal Agent with Antiarrhythmic Properties" *Circulation,* 110(8), 904-910 (2004).
"End of the Road for Eleclazine and Liberty HCM Study," *HCM Beat* (Dec. 27, 2016).
Notice of Discontinuation of a Pediatric Development which is Covered by an Agreed PIP Decision (Feb. 9, 2017).
Brackenbury et al., "Activity-dependent regulation of voltage-gated Na+ channel expression in Mat-LyLu rat prostate cancer cell line", Journal of Physiology 573.2, 2006, pp. 343-356.
Chioni et al., "Protein kinase A and regulation of neonatal Nav1.5 expression in human breast cancer cells: Activity- dependent positive feedback and cellular migration", The International Journal of Biochemistry and Cell Biology 42, 2010, pp. 346-358.
Driffort et al., "Ranolazine inhibits NaV1.5-mediated breast cancer cell invasiveness and lung colonization", Molecular Cancer, 2014, 13:264, 6 pages.
Kavzan et al., "Immortalized cells and one oncogene in malignant transformation: old insights on new explanation", BMC Cell Biology, 2011, 12:23, 2 pages.

* cited by examiner

TREATMENT OF CANCER AND INHIBITION OF METASTASIS

CROSS-REFERENCE TO RELATED APPLICATIONS

This application is a continuation of U.S. application Ser. No. 16/484,997, filed Aug. 9, 2019 which is a national stage filing under 35 U.S.C. 371 of PCT/EP2018/053457, filed Feb. 12, 2018, which International Application was published by the International Bureau in English on Aug. 16, 2018, and application claims priority from Denmark Patent Application No. PA 2017 70091, filed Feb. 10, 2017, which applications are hereby incorporated in their entirety by reference in this application.

FIELD OF THE INVENTION

This invention relates to the treatment of cancer, and relates particularly to all cancers found to express a voltage-gated sodium channel (VGSC), such as, but not exclusively, treatment of metastatic cancer, such as breast, ovarian, colon or prostate cancer.

BACKGROUND OF THE INVENTION

Metastatic disease is responsible for more than 90% of all cancer-related deaths. Progression of metastatic cancer, such as breast, colon and prostate cancer, is generally considered as comprising five phases, as follows:

1. Genesis, namely the initial transformation of a normal cell into a cancer cell;
2. Proliferation, namely increase in the number of cancer cells to form a primary tumour of increasing size;
3. Switching, during the genesis or proliferation phase, from a condition in which the cancer cells have no potential for metastatic behaviour to a condition in which they do;
4. Detachment of cancer cells from the primary tumour followed by movement of those detached cells into surrounding regions of tissue within the same organ towards the circulation system;
5. Metastasis, namely the movement of the detached cells through the circulation (blood or lymph) to other organs to create secondary tumours in those other organs.

A significant change which takes place in the cell and cause the switch in condition at phase 3 above is the expression of a functional voltage-gated sodium channel (VGSC). In humans, there are nine different VGSC alpha subunit or "NaV" proteins (Nav1.1 to Nav1.9) and all have been found to be expressed on different types of cancer cells (Brackenbury, 2012; Roger et al., 2015). In breast and colon cancers it is typically the Nav1.5 channel which is expressed and in the case of prostate cancer it is typically the Nav1.7 channel. VGSCs may be expressed in neonatal and/or adult form. In the case of breast and colon cancer, it is the neonatal form of the Nav1.5 channel (nNav1.5) which is expressed. In the case of prostate cancer, also, it is the neonatal splice variant of Nav1.7 that is expressed (Diss et al., 2001). In the absence of such channels, the tumour cells do not have the potential for invasion and hence metastatic behaviour.

In some cases, the genesis phase involves the growth of cancer cells which, from the outset, have metastatic potential. Further, haematological cancers such as leukaemia have inherent metastatic features and may invade and accumulate in other organs, like the liver or spleen (Trendowski, 2015).

It has been suggested to try to find a treatment for preventing metastasis by one or more of preventing the expression of functional VGSCs, completely blocking the activity of functional VGSCs which have been expressed, or killing the cells. The present invention relates to a different approach.

Current flows intermittently through VGSCs, that is to say the current flows in pulses. It is known that each pulse comprises a transient (or peak) part which is followed by a low-level DC part, known as the late or persistent current. The latter is promoted by hypoxia, well-known to occur in growing tumours. VGSC activity increases invasiveness by promoting proton efflux and acidifying the pericellular space. VGSCs also control pain sensation.

Eleclazine, 4-(pyrimidin-2-ylmethyl)-7-(4-(trifluoromethoxy)phenyl)-3,4-dihydrobenzo[f][1,4]oxazepin-5(2H)-one, of the formula Ia Ia

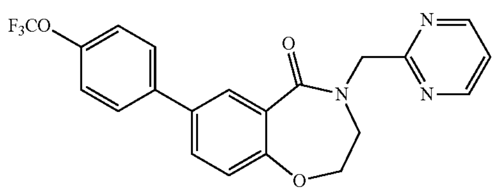

and 4-(pyrimidin-2-ylmethyl)-7-(4-(trifluoromethyl)phenyl)-3,4-dihydrobenzo[f][1,4]oxazepin-5(2H)-one, of the formula Ib Ib

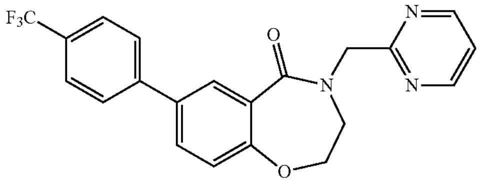

are both known for the treatment of cardiac conditions. It is further known that each of them differentially affects the magnitude of the transient and persistent parts of the VGSC currents, the effect being in a dose-dependent manner. High doses of these drugs completely block the VGSC currents. Doses of these, or any other drug, which would have the effect of completely blocking VGSC currents in cardiac tissue would be fatal to the patient because the heart requires these currents in order to carry out its function. It is further known that the compound of formula Ia and Ib are potent and selective inhibitors of the cardiac late sodium current ($I_{NaL}$), also referred to as the persistent sodium current (INaP), and are effective in treating long QT syndrome in humans; specifically long QT syndrome Type 3 (LQT3), cf. US 2015/0038489 A1.

SUMMARY OF THE INVENTION

The present invention is based, at least in part, on the finding that:

(i) inhibiting the persistent part of the Nav1.5 and Nav1.7 currents in breast and colon cancer and in prostate cancer, respectively, inhibits metastatic behaviour;

(ii) it is not necessary to inhibit the transient part of these currents in order to inhibit metastatic behaviour;

(iii) appropriate doses of a compound of the formula I as defined below will inhibit metastatic behaviour without preventing proliferation or destroying the cells of the tumour; and (iv) the inhibiting effects of a compound of the formula I on the persistent part of the current are greater in cells with prior exposure to hypoxia, which is a condition that occurs in growing tumours and makes a critical positive contribution to the metastatic process.

So, in a first aspect the present invention relates to a compound of the formula I:

I

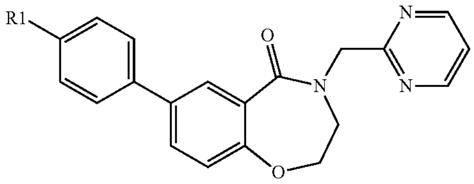

wherein R1 is trifluoromethoxy or trifluoromethyl, or a pharmaceutically acceptable salt thereof, for use in a method of reducing or preventing metastatic behaviour and/or pain sensation in a patient suffering from cancer. In one embodiment, the cancer is a voltage gated sodium channel (VGSC)-expressing cancer. In another embodiment, the cancer is not a VGSC-expressing cancer. For example, the patient may be suffering from a cancer associated with a risk for VGSC-expression and/or metastatic behaviour, but VGSC-expression and/or metastatic behaviour has not yet been determined.

In an embodiment of the invention, R1 in the compound of the formula I is trifluoromethoxy, i.e. the compound of the formula I is eleclazine, 4-(pyrimidin-2-ylmethyl)-7-(4-(trifluoromethoxy)phenyl)-3,4-dihydrobenzo[f][1,4]oxazepin-5(2H)-one, of the formula Ia Ia

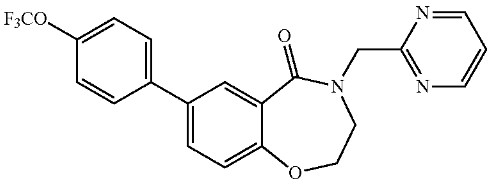

In another embodiment of the invention, R1 in the compound of the formula I is trifluoromethyl, i.e. the compound of the formula I is 4-(pyrimidin-2-ylmethyl)-7-(4-(trifluoromethyl)phenyl)-3,4-dihydrobenzo[f][1,4]oxazepin-5(2H)-one, of the formula Ib Ib

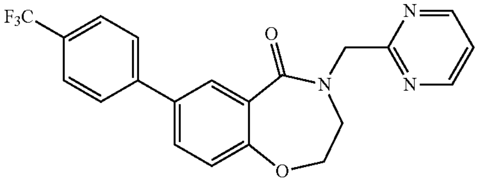

In one embodiment of the invention, the cancer is a non-solid tumour cancer. In one particular embodiment, the cancer is leukaemia. In another particular embodiment, the cancer is lymphoma.

In one embodiment of the invention, the cancer is a solid tumour cancer, such as a carcinoma, mesothelioma, sarcoma, melanoma or a neuroblastoma. In a particular embodiment, the cancer is breast cancer. In another particular embodiment, the cancer is colon cancer. In another particular embodiment, the cancer is prostate cancer. In another particular embodiment, the cancer is non-small cell lung cancer (NSCLC). In another particular embodiment, the cancer is cervical cancer. In another particular embodiment, the cancer is gastric cancer. In another particular embodiment, the cancer is neuroblastoma.

In accordance with one embodiment of the invention, the cancer is in phase 3, 4, or 5. In accordance with another embodiment of the invention, the cancer is in phase 1 or 2.

In accordance with an embodiment of the invention, metastatic behaviour is inhibited or reduced in cancer by administering a compound of the formula I, i.e., either Ia or Ib, at an appropriate dosage in a patient suffering from voltage gated sodium channel (VGSC) expressing cancer.

In accordance with a further embodiment of the invention, metastatic behaviour is inhibited or reduced in cancer by administering a compound of the formula I at an appropriate dosage to inhibit or reduce the persistent part of the VGSC current without blocking, or at least without completely blocking, the transient part. Thus, metastasis in cancer may be inhibited or reduced in this way without having to administer doses of drugs which would be fatal.

In accordance with a further embodiment of the invention, which will be more fully explained below, a compound of the formula I is administered at a dosage level which will inhibit the persistent part of the VGSC current without blocking or completely blocking the transient part and without directly causing cell death. Thus, the tumour or metastasis may be inhibited without causing the death of the cancer cell.

The fact that metastatic behaviour may be inhibited or reduced without causing cell death may be a significant advantage since recent work has suggested that treating cancer by killing the cells may, at least in some cases, be counterproductive in the sense that whilst there will be a short-term benefit, the cancer will nevertheless return and proliferate. Thus, the invention provides the possibility of inhibiting or preventing metastatic behaviour without the potential problems which may arise from actually killing the cancer cells.

In accordance with one embodiment of the invention, the metastatic behaviour is reduced or prevented by:

(a) reducing the invasiveness of cancer cells;

(b) reducing the motility of cancer cells, optionally under hypoxic but not normoxic conditions;

(c) decreasing cancer cell expression of at least one VGSC, optionally under both normoxic and hypoxic conditions;

(d) increasing the adhesiveness of cancer cells;

(e) reducing the ability of cancer cells to migrate; or (f) a combination of (a) and (b), (b) and (c), (a) and (c), (a) to (c), or (a) to (e).

The compound is typically administered at a therapeutically effective dose. Embodiments pertaining to specific dosage regimens are described in more detail below. In a particular embodiment, the compound is administered at a dosage or dosage regimen providing for a reduction or prevention of a metastatic behaviour in accordance with any one of (a) to (f) above.

In accordance with a further embodiment of the invention, the compound of the formula I is used at a dosage level corresponding to the range 1 μmol to 10 μmol.

These and other aspects and embodiments of the invention are further described below, with reference to the accompanying drawings and experimental data set out in the Examples.

BRIEF DESCRIPTION OF THE DRAWINGS

FIG. 10A shows the standard curve. The total cell number (per well) linearly increases with absorbance readings (570 nm). The background reading of 0.04 (empty well) was subtracted from all data sets. FIG. 10B reports normalised data showing the proliferation of MDA-MB-231 cells over 48 hours in hypoxic and normoxic conditions. Eleclazine and ranolazine were administered at a concentration of 10 μM. DMSO (0.2%), TTX (10 μM) and media were negative controls. 2 mM TEA (K+ channel blocker) served as a positive control.

DETAILED DISCLOSURE OF THE INVENTION

Metastatic behaviour involves several stages, namely:

(a) detachment of cells from the tumour;

(b) movement of the detached cells into the surrounding tissue;

(c) movement through that surrounding tissue towards the circulation system; and (d) movement into the circulation system (from which the cells may exit ultimately to form secondary tumours).

Inhibiting or reducing the activity of the cells in any one or more of these stages will therefore contribute to at least a reduction in metastasis. The effect of drugs on each of these sub-stages can be determined, as more fully explained below, by a number of experiments, namely:

(a) testing the effect of the drug on the adhesiveness of the cells;

(b) testing the effect of the drug on the lateral motility of the cells;

(c) testing the effect of the drug on the transverse migration of the cells; and (d) testing the effect of the drug on the invasiveness of the cells, namely the ability of the cells to move through a medium which is consumed by the cells.

Administering a compound of the formula I in various dosage levels can increase the adhesiveness of the cells and/or reduce one or more of the lateral motility, transverse migration and invasiveness of the cells.

Accordingly, in accordance with another aspect of the invention, a compound, composition or other substance is provided which is used or intended to be used, in an appropriate dose, to inhibit or reduce the persistent part of the VGSC current in metastatic cancer cells whilst leaving the transient part unaffected or only partially reduced, for inhibiting or reducing metastasis, preferably without directly causing cell death.

Advantages that flow from the invention, at least in certain aspects or forms, include the following:

According to the invention, breast, colon and prostate cancer (and other cancers in which VGSCs are expressed or may become expressed, as described herein) can be contained so that the patient may be able to live with such cancer without serious detriment. As a result, the need for the patient to undergo aggressive treatments to destroy the cancerous cells, such as by chemo or radiotherapy may be avoided. If a patient is suspected of having breast, colon or prostate cancer or other metastatic cancer, immediate treatment with appropriate doses of a compound of the formula I can be given to inhibit or prevent metastasis whilst awaiting the results of definitive tests. The dosage necessary to achieve this only has to be high enough to inhibit the persistent part of the VGSC current. Therapeutically acceptable doses of a compound of the formula I will achieve the required inhibition of the persistent part of these currents, whilst leaving the transient part substantially unaffected.

Figure 1:
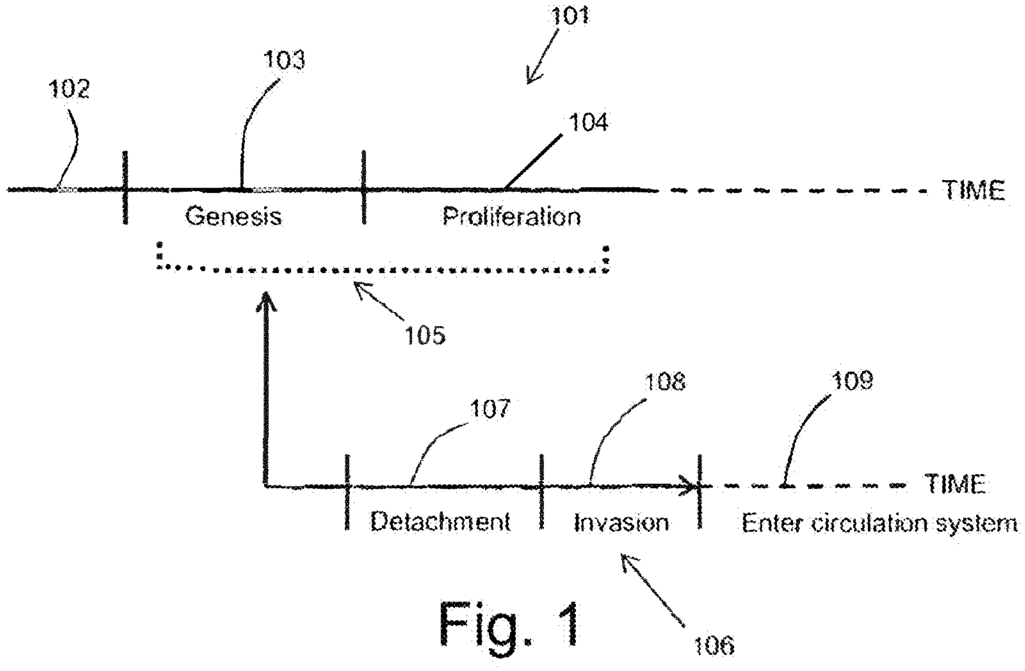
FIG. 1 is a schematic representation of a timeline for cancer progression from primary tumorigenesis to formation of secondary tumours (metastases).

With reference to FIG. 1, timeline 101 is a representation of three successive phases in the development of a tumour, namely a phase 102 prior to the development of cancerous cells, a phase 103 following phase 102 during which the genesis of cancer cells takes place and a phase 104, following phase 103, during which the cancerous cells proliferate so as to form a growing tumour. The proliferation phase 104 may begin soon after the genesis phase 103 begins.

It has been established that many human cancer cells, such as those of breast, colon and prostate cancer, may initially not include any functional VGSCs and that, unless such channels are expressed in the tumour, the tumour cells will not be invasive. However, in many such tumours, even though initially there are no VGSC's, at some point functional VGSC's will be expressed. This triggers a change to a condition in which the tumour may spread. FIG. 1 represents a situation in which initially the cells do not contain any functional VGSC's but at some point in time 105 the expression of functional VGSC begins. This may occur at any time after commencement of the genesis phase 103.

Timeline 106 in FIG. 1 illustrates the phases which arise following time 105, when the cancer becomes metastatic. In the first phase 107 following time 105, metastatic cells detach themselves from the tumour. Thereafter, in phase 108, they invade and move through surrounding tissue in the same organ towards the circulation system, in particular the vascular and/or the lymphatic system. In phase 109, the metastatic cells enter the circulation system which may then carry them to other organs in the body, at which they may cause the formation of secondary tumours.

Figure 2:
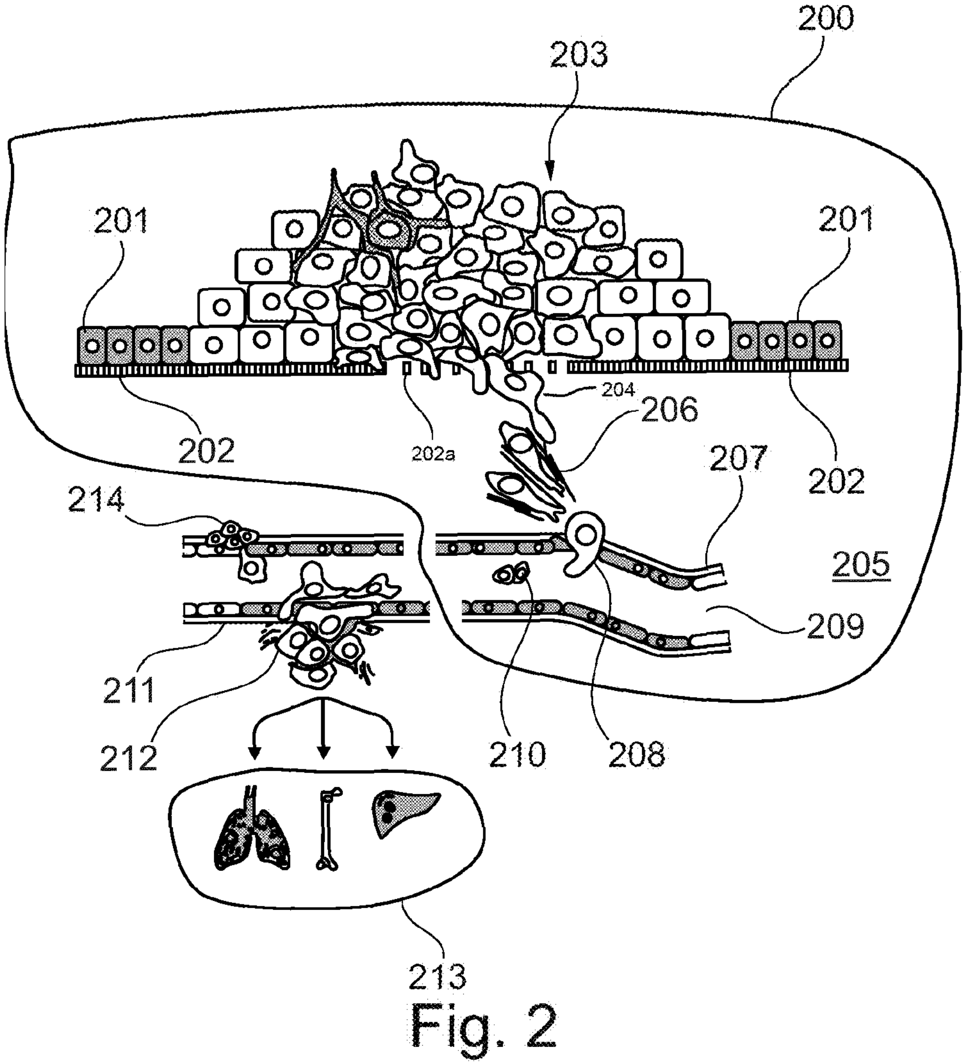
FIG. 2 is a schematic illustration of the cellular processes occurring during cancer initiation and progression to metastasis.

The above phases are pictorially represented in FIG. 2 in which reference number 200 represents a portion of an organ such as a breast or a prostate. Healthy cells 201 of the breast or prostate are shown as supported on a basement membrane 202 and surrounding a cancerous tumour 203, which is assumed to have gone through the genesis phase 103 and into the proliferation phase 104.

Certain cells 204 of the cancerous tumour 203 are shown as detaching from the tumour 203 and passing through a degraded region 202*a* of the basement membrane 202 into adjacent region 205 of the organ containing the tumour 203, which region may comprise mainly collagen fibres. Cancer cells 206, which have become detached from the tumour and have passed through the basement membrane 202, are shown passing through the region 205 towards a blood vessel 207. A cancerous cell 208 is shown migrating through the wall of the blood vessel 207 into the bloodstream 209.

Cells 210, which have already entered the bloodstream, are shown as being carried within the bloodstream to a region 211 where cells 212 are shown as having migrated outwardly through the wall of the blood vessel 207 towards another organ 213, such as the lymph glands or liver, in which they may form a secondary tumour (not shown).

Reference number 214 represents dormant cancerous cells which have simply settled in or adjacent to the wall of the blood vessel 207.

As more fully explained below, the invention provides a treatment or means for preventing or reducing one or more of the metastatic behaviours of the cancer cells which takes place in the various phases described. In particular, the invention provides a treatment or means for:

(a) increasing the adhesiveness of the cells in the tumour so that they are less likely to detach; and/or (b) reducing the motility of the cells which have become detached so they are less likely to move to and through the basement membrane into the surrounding tissue; and/or (c) reducing the invasiveness of the cells which have entered the surrounding tissue by reducing their ability to move through that tissue towards the circulation system; and/or (d) reducing the ability of the cells to migrate from that tissue into the circulatory system via the walls thereof.

It has been explained above that cancerous cells which do not have functional VGSCs expressed therein do not behave invasively. Further, it is known that current passes through VGSCs in pulses, each of which comprises a transient or peak part followed by a much lower level persistent or late part. In accordance with an aspect of the invention, one or more of the above metastatic behaviours is inhibited or reduced by inhibiting or reducing the persistent part of the current whilst not eliminating the peak part, so making it possible to use a drug which will preferentially reduce the persistent part of the current.

Some such drugs are known for treating heart conditions such as arrhythmia or angina. In the case of treating the heart, it is vital to ensure that the peak part of the current is not eliminated because this is essential to maintain the functionality of the heart and its rhythm. Thus, in accordance with an aspect of the invention a known drug, such as a compound of the formula I, previously described for use for inhibiting or reducing the persistent part of the VGSC current without eliminating the peak part is used for inhibiting or reducing metastatic behaviour in cancer, especially breast, colon or prostate cancer.

The nature of the VGSC current will be further described with reference to FIG. 3.

Figure 3:
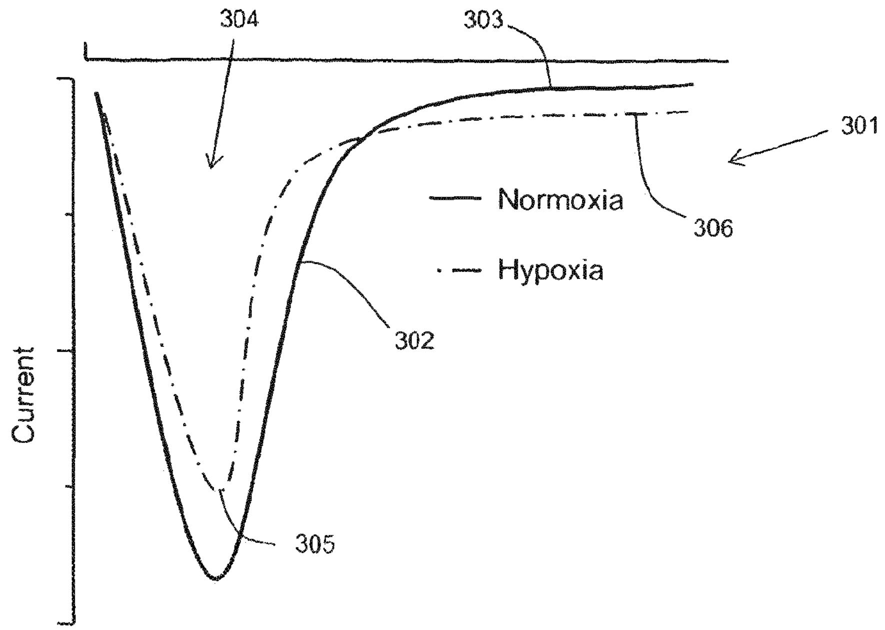
FIG. 3 is a sketch illustrating the current through VGSC's, showing both the transient and persistent parts of the current and also showing the current under both normoxic and hypoxic conditions.

Referring to FIG. 3, curve 301, shown as an unbroken line, represents a current pulse flowing through functional VGSC under normoxic conditions, the horizontal axis being time and the vertical axis being amplitude or magnitude of the current. As can be seen, this current pulse comprises a peak or transient portion 302 and the persistent or late portion 303. In practice, the time period for which the persistent part 303 persists is very much greater than the time period of the transient part 302 although, since FIG. 3 is a diagrammatic sketch rather than a curve actually obtained from experimental data, this is not shown in the figure.

Curve 304, drawn in chain dotted lines, shows a pulse of VGSC current under hypoxic conditions. As can be seen, the peak part 305 of the current under hypoxic conditions is smaller than the peak part 301 under normoxic conditions, but the persistent part 306 under hypoxic conditions is greater than the persistent part 303 under normoxic conditions. The difference between these curves under hypoxic and normoxic conditions is relevant, because many of the cells in a cancerous tumour are hypoxic due to their partial isolation, by other cancerous cells, from the blood circulation system.

Definitions

"Voltage-gated sodium channels" or "VGSCs" is a known class of integral membrane proteins that form ion channels, conducting sodium ions (Na+) through a cell's plasma membrane. In humans, there are nine genes (SCN1A, SCN2A, SCN3A, SCN4A, SCN5A, SCN8A, SCN9A, SCN10A, and SCN11A) which encode for nine different VGSC alpha subunit or "NaV'" proteins (Nav1.1 to Nav1.9, respectively). As used herein, unless contradicted by context, the term may refer to any and all known VGSCs including, but not limited to Nav1.5 (SCN5A) (in neonatal or adult form), Nav1.6 (SCN8A), and Nav1.7 (SCN9A) (Fraser et al., 2005; Djamgoz et al., 2011). Nav1.5 may alternatively be denoted NAV-1.5 herein.

As used herein, "treatment" of a cancer includes, but is not limited to, reducing metastatic behaviour of a cancer, preventing metastatic behaviour of a cancer, reducing pain sensation, or any combination thereof.

By "therapeutically effective amount" or "therapeutically effective dose", it is intended an amount or dosage of compound of Formula I, that when administered to a patient suffering from cancer brings about a positive therapeutic response with respect to treatment of the patient, such as, e.g., reduction of metastatic behaviour of the cancer, prevention of metastatic behaviour of the cancer, reduction of pain, or the like.

By "reducing metastatic behaviour" of cancer, it is intended a reduction of any behaviour associated with the movement of detached cancer cells through the circulation (blood or lymph) to accumulate and/or create secondary tumours in other organs or locally invade surrounding tissues. Typically, the patient is in phase 3, 4 or 5, such as in phase 4 or 5. Reducing metastatic behaviour may, for example, include one or more of (i) reducing cancer cell motility (e.g., reduced lateral motility), (ii) reducing cancer cell migration (e.g., transverse migration), (iii) reducing cancer cell adhesiveness, (iv) reducing cancer cell invasiveness, (v) reducing the persistent part of the VGSC current without eliminating the transient part, and (vi) reducing expression of at least one VGSC on cancer cells, as compared to a control. The VGSC may, for example, be one or more of Nav1.5 (in adult and/or neonatal form), Nav1.6 and Nav1.7. As explained elsewhere herein, "motility" reflects the ability of the tumour cells to initially move to and through the basement membrane into the surrounding tissue; "invasiveness" of the cells reflects the ability of tumour cells which have entered the surrounding tissue to move through that tissue towards the circulation system; and "migration" reflects the ability of the tumour cells to migrate from that tissue into the circulatory system via the walls thereof.

By "preventing metastatic behaviour" of cancer, it is intended to refer prophylactic treatment of a cancer patient at risk for, but not yet diagnosed with, a metastatic disease, so as to prevent or reduce the risk for a metastatic behaviour of the cancer as described above. Typically, the patient is in phase 1, 2 or 3. Preventing metastatic behaviour may, for example, include preventing or reducing the expression of at least one VGSC, such as e.g., one or more of Nav1.5 (in adult and/or neonatal form), Nav1.6 and Nav1.7.

Haematological cancer do not as such form metastases in the way solid tumour cancers do, but are characterized by metastatic behaviour in that haematological cancer cells may invade and accumulate in other organs. Accordingly, in the present disclosure, any embodiment concerning "preventing a metastatic behaviour" or "reducing the metastatic behaviour" can, particularly in the context of a haematological cancer, alternatively be expressed as "preventing invasive behaviour" and "preventing invasive behaviour".

Specific Embodiments of the Invention

As shown in present Example 2, a compound according to Formula I (eleclazine) tested on breast cancer cells had no effect on cell viability (20 microM); had no effect on cells' proliferative activity (10 microM); reduced lateral motility under hypoxic but not normoxic conditions; significantly suppressed the Matrigel invasiveness at clinically relevant concentrations (<10 microM; concentration-dependent); appeared, at least at some concentrations, more effective than a reference compound (5 microM); and reduced the expression of neonatal Nav1.5 protein under both normoxic and hypoxic conditions (10 microM). Further, as shown in Example 3, a compound according to Formula I (Eleclazine) had anti-invasive effects of eleclazine and ranolazine on a human leukaemic cell line.

Compound

The present invention relates to a compound of the formula I, wherein R1 is trifluoromethyl or trifluoromethoxy, or a pharmaceutically acceptable salt thereof, for use in a method of treating cancer in a patient suffering from cancer, particularly by reducing metastatic behaviour of a cancer, preventing metastatic behaviour of a cancer and reducing the pain sensation in a cancer.

In some embodiments, R1 is trifluoromethyl and the compound is 4-(pyrimidin-2-ylmethyl)-7-(4-(trifluoromethoxy)phenyl)-3,4-dihydrobenzo[f][1,4]oxazepin-5 (2H)-one (i.e., eleclazine), or a pharmaceutically acceptable salt thereof. In some embodiments, R1 is trifluoromethyl, and the compound is 4-(pyrimidin-2-ylmethyl)-7-(4-(trifluoromethyl)phenyl)-3,4-dihydrobenzo[f][1,4]oxazepin-5 (2H)-one, or a pharmaceutically acceptable salt thereof.

In separate and specific embodiments, the compound is not cytotoxic to cancer cells, does not substantially affect proliferation of cancer cells, and/or has the effect of at least reducing the persistent part of the voltage gated sodium channel current without eliminating the transient part, preferably at therapeutically effective concentrations, i.e., concentrations where the compound reduces one or more metastatic behaviours of the cancer cells. That is to say, the cancer cells them self are unaffected other than they are inhibited from growing and expanding into the surrounding tissue, by degradation of the tissue caused by the VGSC mechanism. The proliferation itself is not substantially affected.

Suitable salts of a compound according to Formula I, such as Ia and Ib, are described in US 2017/007617 A1. In particular, such salts include pharmaceutically acceptable salts that are safe for administration to a patient and which preserve the biological effectiveness and properties of the compound. Pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines. Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

In accordance with one embodiment of the invention, the compound of formula I is selective on one or more VGSCs, such as selective on one, two, three, four, five, six, seven, eight or all of NAV-1.1 to 1.9. In some embodiments, the compound of formula I is selective on at least NAV-1.5, NAV-1.6 and NAV-1.7. In one embodiment of the invention, the compound of the formula I is selective on nNAV-1.5 over adult NAV-1.5.

Therapeutic Applications

Suitable patients include mammalian patients, such as humans, monkeys, rabbits, dogs, cats, cows, horses, pigs, mice and rats, suffering from cancer. Preferably, the patient is a human patient, such as an adult human patient. Typically, such an adult human patient may have a weight in the range of about 50 to about 150 kg, such as about 60 to about 100 kg, such as about 70 kg.

Typically, a cancer selected for treatment according to the invention is a VGSC-expressing cancer or a cancer associated with a known risk for VGSC expression and thereby metastatic behaviour.

In some embodiments, the cancer is a haematological cancer such as leukaemia or lymphoma. In some embodiments, the cancer is a solid tumour cancer, such as, e.g., a carcinoma, mesothelioma, sarcoma, or melanoma. In particular embodiments, the solid tumour cancer is breast cancer, colon cancer, prostate cancer, lung cancer (e.g., non-small cell lung cancer; NSCLC), pleural cancer (e.g., mesothelioma), cervical cancer, ovarian cancer, gastric cancer or neuroblastoma. In one specific embodiment, the cancer is leukaemia. In another specific embodiment, the cancer is breast cancer.

Table 1 below shows links that have been found between some particular cancer forms and their VGSC expression.

TABLE 1

| CARCINOMA | VGSC SUBTYPE(S) |
|---|---|
| Breast | Nav1.5 |
| Colon | Nav1.5 |
| Prostate | Nav1.7 and/or Nav1.6 |
| NSCLC | Nav1.7 |
| Cervical | Nav1.6 |
| Gastric | Nav1.7 |
| Ovarian | Nav1.5 |
| Neuroblastoma | Nav1.5 |
| Astrocytoma | Nav1.5 |
| Leukaemia | Nav (subtype(s) not determined) |
| Melanoma | Nav (subtype(s) not determined) |

In some embodiments, the patient is suffering from a VGSC-expressing cancer. A VGSC-expressing cancer may, for example, be identified by immunohistochemical or analysis of a cancer cell-containing sample (such as a tumour biopsy or blood sample) obtained from the patient, using detectable monoclonal or polyclonal antibodies specific for one or more VGSCs to detect the expression of a VGSC on the cancer cells.

A VGSC-expressing cancer may express any one or more of Nav1.1 to Nav1.9, in adult or neonatal form. In one embodiment, the cancer expresses at least one of Nav1.5, Nav1.6 and Nav1.7, in adult and/or neonatal form. In a specific embodiment, the cancer expresses Nav1.5, in adult and/or neonatal form, such as, e.g., neonatal Nav1.5. In another specific embodiment, the cancer expresses Nav1.6, in adult or neonatal form, such as neonatal form. In another embodiment, the cancer expresses Nav1.7, in adult or neonatal form, such as neonatal form.

A VGSC-expressing cancer is in phase 3, 4 or 5 as described above.

In one embodiment, the patient is in stage 3, 4 or 5, such as in phase 4 or 5. In one embodiment, the cancer is in stage 1, 2, or 3, such as in phase 1 or 2.

In one embodiment, the cancer is in phase 3. A patient suffering from a cancer in phase 3 has typically not been diagnosed with metastatic disease, but is at risk for metastatic behaviour of the cancer, i.e., progression to phase 4 or 5. A patient suffering from a cancer in phase 3 may thus be treated according to the invention to prevent metastatic behaviour of the cancer.

In one embodiment, the cancer is in phase 4. A patient suffering from a cancer in phase 4 may not have been diagnosed with metastatic disease, but the cancer has progressed towards metastatic behaviour. A patient suffering from a cancer in phase 4 may thus be treated according to the invention to reduce metastatic behaviour of the cancer.

In one embodiment, the cancer is in phase 5. A patient suffering from a cancer in phase 5 may have been diagnosed with metastatic disease, and the cancer is characterized by metastatic behaviour. A patient suffering from a cancer in phase 5 may thus be treated according to the invention to reduce metastatic behaviour of the cancer.

In some embodiments, the patient may be suffering from a cancer associated with a risk for VGSC-expression and/or metastatic behaviour, but VGSC-expression and/or metastatic behaviour has not yet been determined. Cancers that are prone to metastatic behaviour include, for example, leukaemia, breast cancer, colon cancer, prostate cancer, lung cancer (e.g., non-small cell lung cancer; NSCLC), pleural cancer (e.g., mesothelioma), cervical cancer and ovarian cancer (Roger et al., 2015). For example, an immunohistochemical analysis of a cancer cell-containing sample such as a tumour biopsy or blood sample obtained from the patient may have indicated that the tumour cells in the sample did not express the VGSC or VGSCs tested for. The cancer may thus be in phase 1 or (more likely) in phase 2.

In one embodiment, the cancer is in phase 2. A patient suffering from a cancer in phase 2 has typically not been diagnosed with metastatic disease, but is at risk for VGSC expression and metastatic behaviour of the cancer, i.e., progression to phase 3, 4 or higher. A patient suffering from a cancer in phase 2 may thus be treated according to the invention to prevent VGSC-expression or metastatic behaviour of the cancer.

A patient suffering from a cancer in any one of phase 1-5, preferably in any one of 2-5, may also suffer from pain caused by the cancer, e.g., by a primary tumour, and may thus be treated according to the invention to reduce pain sensation.

In one embodiment, when used in a method according to the invention, the compound reduces or prevents metastatic behaviour in VGSC expressing cancer without killing the cancer cells.

In one embodiment, when used in a method according to the invention, the compound reduces or prevents metastatic behaviour in VGSC expressing cancer without substantially affecting proliferation of the cancer cells.

In one embodiment, when used in a method according to the invention, the compound reduces or prevents metastatic behaviour in VGSC expressing cancer by the effect of at least reducing the persistent part of the VGSC current without eliminating the transient part. Suitable assays for evaluating the effect of the compound on the VGSC current are known in the art (see, e.g., Rajamani et al., 2016).

In other separate and specific embodiments, the compound reduces or prevents metastatic behaviour by:

(a) reducing the invasiveness of cancer cells;

(b) reducing the motility of cancer cells, optionally under hypoxic but not normoxic conditions;

(c) decreasing cancer cell expression of at least one VGSC, optionally under both normoxic and hypoxic conditions;

(d) increasing the adhesiveness of cancer cells;

(e) reducing the ability of cancer cells to migrate; or (f) a combination of (a) and (b), (b) and (c), (a) and (c), (a) to (c), or (a) to (e).

In one embodiment, the at least one VGSC comprises one, two or all of Nav1.5, Nav1.6 and Nav1.7. In one embodiment, the at least one VGSC comprises or consists of neonatal Nav1.5.

In one embodiment, treatment of cancer cells with the compound results in cancer cell expression of the at least one VGSC being significantly lower than that of a control, such as a predetermined control value, cancer cells not exposed to the compound or cancer cells exposed to a reference compound. In one embodiment, treatment of cancer cells with the compound results in the invasiveness, motility and/or ability to migrate of cancer cells treated with the compound being significantly lower than that of a control, such as a predetermined control value, cancer cells not exposed to the compound or cancer cells exposed to a selected reference compound.

Assays for evaluating (a) to (d) are known in the art and described below and in the Examples.

Administration Modes

The compound can be administered by any suitable route to the patient, including, but not limited to, oral, buccal, sublabial, sublingual, rectal, intravenous, subcutaneous, intradermal, intramuscular, transdermal and intranasal administration and/or direct administration to a tumour, such as a primary tumour. Preferably, the compound is administered orally, e.g., as a tablet or capsule. In some cases, the tablet or capsule may be formulated or coated so that the compound is not released until it reaches a desired destination, e.g., the stomach. Sustained-release systems may also be used, particularly so as to release the compound over a prolonged period of time.

The compound is typically formulated together with one or more pharmaceutically acceptable excipients, diluents or carriers according to well-known methods in the art. For example, US 2017/0007617 A1 describes suitable formulations of compounds according to Formula I for intravenous administration.

Dosage Regimens

The compound is administered to the patient in a therapeutically effective amount for the intended purpose, and with a frequency and for a period of time determined by a trained physician.

In one embodiment, a therapeutically effective dose is one that results in a plasma concentration, preferably steady-state, of the compound of from about 0.01 μM to about 10 μM. Accordingly, in some embodiments, the compound is administered so as to achieve a steady-state plasma concentration of from about 0.01 μM to about 10 μM, such as about 1 μM or 5 μM.

In one embodiment, the compound is administered at a dosage of about 1 mg to about 30 mg, such as from 1 to about 15 mg, such as from about 1 to 10 mg, such as from about 1 mg to about 5 mg, such as from about 2 mg to about 4 mg to the patient, such as an adult human patient. In another embodiment, the compound is administered at a dosage of about 5 to about 15 mg, such as from about 10 mg to about 15 mg, such as from about 12 to about 14 mg to the patient, such as an adult human patient. In another embodiment, the compound is administered at a dosage of about 8 mg to about 13 mg to the patient, such as an adult human patient.

In one embodiment, the compound is administered at a dosage of about 1 mg, 3 mg, about 6 mg, about 9 mg, about 12 mg, about 15 mg, about 18 mg, about 21 mg, about 24 mg, about 27 mg, or about 30 mg to the patient, such as an adult human patient In one embodiment, the compound is administered once daily, once every two days, once every 3 days, once every 5 days, once every week, once every two weeks, or once monthly, such as once daily. Preferably, the compound is administered once daily, preferably orally (perorally (p.o)), for maintenance therapy.

In one embodiment, the compound is administered as a maintenance therapy over a period of at least 4 weeks, such as at least 8 weeks, such as at least 12 weeks, such as at least 24 weeks, such as at least 48 weeks, or more.

In one embodiment, before the start of the maintenance therapy, e.g., one or two days before, a one-time initial boost dose of the compound is administered of from about 10 mg to about 100 mg, such as from about 20 mg to about 80 mg, such as from about 30 mg to about 70 mg, such as from about 40 mg to about 60 mg, such as about 30 mg, about 50 mg, about 80 mg, about 90 mg, or about 95 mg to the patient, such as an adult human patient.

Without being limited to theory, from current knowledge of eleclazine pharmacokinetics, the daily dosage for a maintenance therapy according to the invention using, e.g., a compound according to Formula Ia (eleclazine, 451.83 g/mol; PubChem CID: 71183216) following an initial boost dose of about 95 mg and providing for a desired concentration in the order of about 5 μM in an adult human patient (assumed to have a weight of about 70 kg and a distribution volume of about 42 litre) can be estimated as follows:

| | | | | |
|---|---|---|---|---|
| Eleclazine half-life (days) | 2.5 | 5 | 10 | 15 |
| Daily dose to maintain concentration (mg) | 19 | 9.5 | 4.7 | 3.2 |

Accordingly, in one embodiment, the compound for use according to the invention is first administered orally (p.o.) as a one-time initial boost (or loading) dose of from about 10 mg to about 100 mg, followed by orally administering a dosage from about 1 mg to about 20 mg, such as from about 1 to about 15 mg, once daily for a period of at least 4 weeks.

In one particular embodiment, the compound for use according to the invention is first administered orally (p.o.) as a one-time initial boost (or loading) dose of about 20 to about 100 mg, followed by orally administering a dosage of from about 3 mg to about 20 mg, such as about 3 mg, about 4 mg, about 5 mg, about 6 mg, about 7 mg, about 8 mg, about 9 mg, about 10 mg, about 12 mg, about 15 mg, about 19 mg or about 20 mg once daily, for a period of at least 4 weeks. In separate and specific embodiments, the initial loading dose is about 30 mg, about 50 mg, about 80 mg, and about 95 mg.

In one particular embodiment, the compound for use according to the invention is first administered orally (p.o.) as a one-time initial boost (or loading) does of about 20 to about 100 mg, followed by orally administering a dosage of from about 3 mg to about 10 mg, such as about 3 mg, about 5 mg, about 6 mg, about 9 mg, or about 10 mg once daily, for a period of at least 4 weeks. In separate and specific embodiments, the initial loading dose is about 30 mg, about 50 mg, about 80 mg, and about 95 mg.

In one particular embodiment, the compound for use according to the invention is first administered orally (p.o.) as a one-time initial boost (or loading) dose of about 30 mg to about 100 mg, followed by orally administering a dosage of about 3 mg once daily, for a period of at least 4 weeks. In separate and specific embodiments, the initial loading dose is about 30 mg, about 50 mg, about 80 mg, and about 95 mg.

In one particular embodiment, the compound for use according to the invention is first administered orally (p.o.) as a one-time initial boost (or loading) dose of about 30 mg to about 100 mg, followed by orally administering a dosage of about 5 mg once daily, for a period of at least 4 weeks. In separate and specific embodiments, the initial loading dose is about 30 mg, about 50 mg, about 80 mg, and about 95 mg.

In one particular embodiment, the compound for use according to the invention is first administered orally (p.o.) as a one-time initial boost (or loading) dose of about 30 mg to about 100 mg, followed by orally administering a dosage of about 6 mg once daily, for a period of at least 4 weeks. In separate and specific embodiments, the initial loading dose is about 30 mg, about 50 mg, about 80 mg, and about 95 mg.

In one particular embodiment, the compound for use according to the invention is first administered orally (p.o.) as a one-time initial boost (or loading) dose of about 30 mg to about 100 mg, followed by orally administering a dosage of about 9 mg once daily, for a period of at least 4 weeks. In separate and specific embodiments, the initial loading dose is about 30 mg, about 50 mg, about 80 mg, and about 95 mg.

In one particular embodiment, the compound for use according to the invention is first administered orally (p.o.) as a one-time initial boost (or loading) dose of about 30 mg to about 100 mg, followed by orally administering a dosage of about 10 mg once daily, for a period of at least 4 weeks. In separate and specific embodiments, the initial loading dose is about 30 mg, about 50 mg, about 80 mg, and about 95 mg.

In one particular embodiment, the compound for use according to the invention is first administered orally (p.o.) as a one-time initial boost (or loading) dose of about 30 mg to about 100 mg, followed by orally administering a dosage of about 19 mg once daily, for a period of at least 4 weeks. In separate and specific embodiments, the initial loading dose is about 30 mg, about 50 mg, about 80 mg, and about 95 mg.

In one particular embodiment, the compound for use according to the invention is first administered orally (p.o.) as a one-time initial boost (or loading) dose of about 30 mg to about 100 mg, followed by orally administering a dosage of about 20 mg once daily, for a period of at least 4 weeks. In separate and specific embodiments, the initial loading dose is about 30 mg, about 50 mg, about 80 mg, and about 95 mg.

In another particular embodiment, the compound for use according to the invention is first administered orally (p.o.) as a one-time initial boost (or loading) dose of about 30 mg, followed by orally administering a dosage of about 3 mg or about 6 mg once daily, for a period of at least 4 weeks.

In another particular embodiment, the compound for use according to the invention is first administered orally (p.o.) as a one-time initial boost (or loading) dose of about 48 mg, followed by orally administering a dosage of about 3 mg or about 6 mg once daily, for a period of at least 4 weeks.

In one embodiment, the compound for a use according to the invention is administered at a dosage level corresponding to the range 1 μmol to 10 μmol, corresponding to about 0.45 mg to about 4.5 mg of a compound according to Formula Ia.

Assays

The following are non-limiting examples of assays useful for evaluating the effect of a compound according to the invention on metastatic behaviour or other properties of cancer cells.

Single-Cell Adhesion Assay

Figure 4:
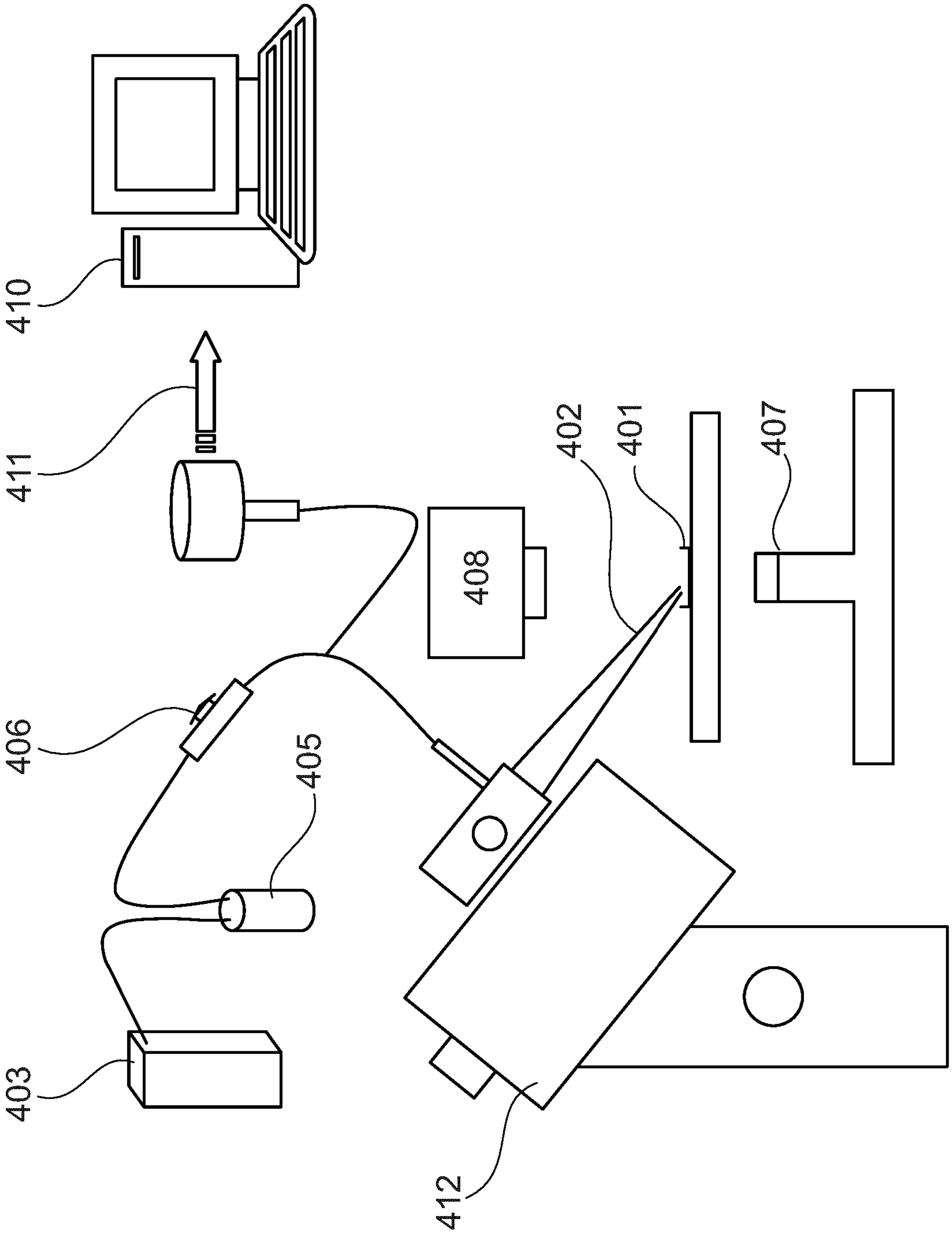
FIG. 4 is a schematic illustration of a cell adhesion measuring apparatus for measuring the adhesion of cells singly.

FIG. 4 is a schematic illustration of the single-cell adhesion measurement apparatus (SCAMA) first described in the paper by Palmer et al. (2008).

Human breast cancer cells from the MDA-MB-231 cell line were plated at a density of $2.5\times10^4$ cells/ml and left to settle in a cell culture dish 401 for 48 hours prior to measurements. Medium was removed and 2 ml of the drug under study was applied for 10 minutes. Adhesion was measured using a glass micropipette 402 connected to a vacuum pump 403 via a plastic tubing. The tip of the micropipette was drawn to about 20 μm (range, 17-24 μm) tip diameter. The vacuum pump was used to create negative pressure inside a reservoir 405 so that the negative pressure could be applied to the tip of the micropipette by pressing the thumb to the open end of a sealable T-piece 406. The cells were observed using a 20× microscope objective 407 under the illumination of a lamp 408. The pressure was measured using a digital manometer connected to a computer 410 via a RS232 cable 411.

Using a micromanipulator 412, the micropipette 402 was positioned on the periphery of a single cell. Upon closing of the T-piece 406, the negative pressure was applied to the cell under investigation and, at the exact moment that the cell was observed to be detached from the culture dish 401, the pressure was released by opening the T-piece 406. The negative pressure required to detach the cell was recorded on the computer as a pressure spike. The peak of the spike ("detachment negative pressure" (DNP)) was used as a measure of the cell's adhesiveness. Using this technique, several recordings could be made from a single dish within minutes.

To simulate hypoxic conditions for the cells, hypoxia was chemically induced by application of hydrogen peroxide (1-500 μM) for the final 24 hours before testing.

In order to test for the reversibility of a given effect, the pharmacological agent was washed off, fresh medium was added and the plate was incubated for a further 10 minutes prior to re-measurement. Each treatment was carried out on at least two dishes of cells, at least 100 cells per dish were measured, and the experiment was repeated three times (with corresponding controls).

Lateral Motility Assay

Figure 5:
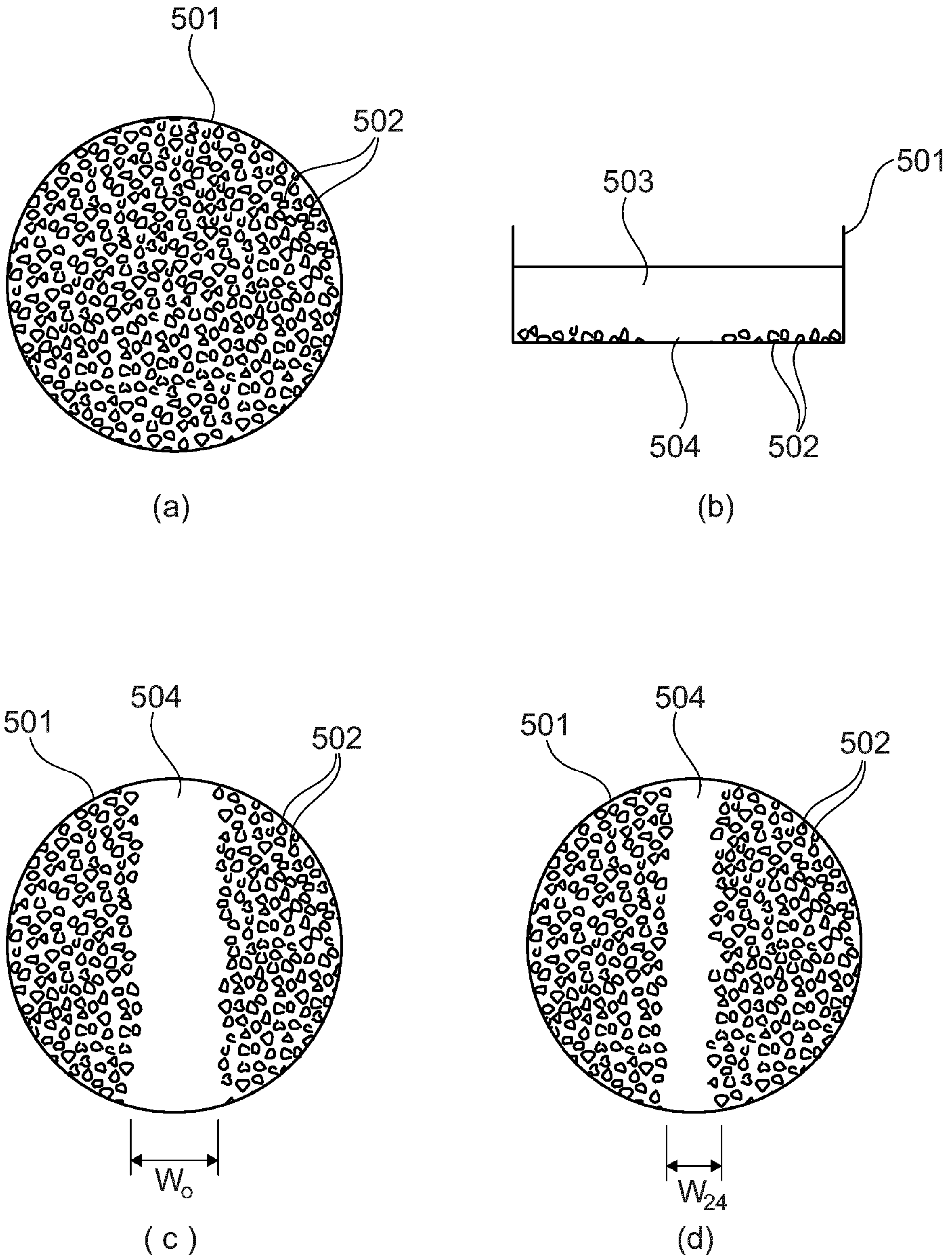
FIG. 5 is a schematic illustration of apparatus used for measuring the lateral motility of cells; view (a) is a plan view from above of a cell culture dish containing a semi-confluent layer of cells; view (b) is a schematic side sectional view of the plated cells; view (c) is a plan view of the plated cells at time t=zero when a scar has been created through the layer of cells, and view (d) is a plan view of the plated cells at a later time (t=24 hours) after the cells have moved and the wound has partially closed.

This assay was used to represent the "free" motility of cancer cells during local spreading. FIG. 5(*a*) is a plan view from above of a cell culture dish 501 having a semi-confluent layer of cells 502 on its surface, the cells being in an aqueous medium 503.

In order to determine lateral motility, a "wound-heal ("scratch")" test was carried out, in which a scratch 504 of −0.5 mm was made through the layer of cells, as shown in FIG. 5(*b*) which is a side sectional view of the cell culture dish. During the period of 24 hours following the formation of the scratch, the cells moved into the gap.

FIGS. 5(*c*) and 5(*d*) are schematic plan views of the cell culture dish 501 at time t=zero when the width of the scratch 504 is w0 and time t=24 hours when the width of the scratch 504 is w24, respectively.

Transverse Migration Assay

Figure 6:
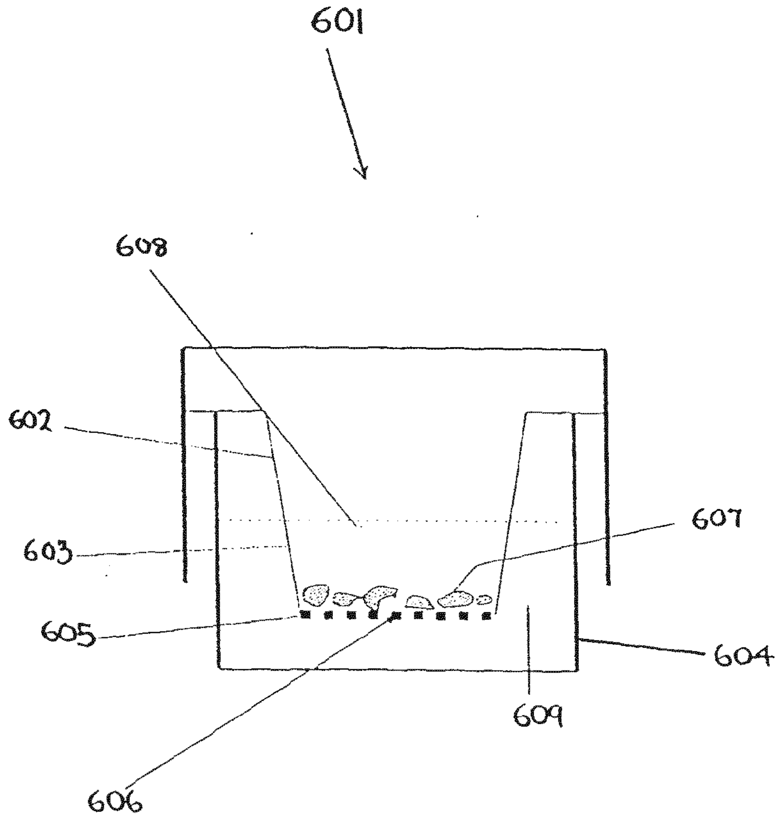
FIG. 6 is a schematic side sectional view of apparatus used for measuring the transverse migration of cells.

This assay was used to represent the ability of cells to migrate as they intra/extravasate. FIG. 6 shows a schematic side sectional view of a migration chamber 601 having a Transwell® insert 602 separating the chamber into two sections which, for convenience, will be referred to as the upper 603 and lower 604 sections of the chamber. The insert 602 has a migration filter membrane 605 in its base with 8 μm pores 606 extending therethrough.

Cells 607 were plated at a density of $2\times10^4$/ml on the filter membrane 605 and placed under a growth medium 608 containing 1% foetal bovine serum (FBS). A chemotactic gradient was created across the filter membrane 605 by placing growth medium 609 containing 10% FBS in the lower section 604 of the chamber.

Cells were allowed to migrate across the filter membrane 605 over a period of 24 hours, cells migrating and adhering to the underside of the filter membrane 605. At the end of each assay, non-migrated cells were removed from the upper surface of the insert 602 with two different swabs The number of cells migrating to the underside of the insert 602 was determined using crystal violet staining. Migrated cells were fixed for 15 minutes with ice-cold methanol. Then 0.5% crystal violet (in 25% methanol) was added for 15 minutes. The inserts were swabbed again and then washed in water and allowed to dry. Cells were then counted using twelve separate fields of view per insert (×200 magnification).

Invasion Assay

This assay is an extension of the transverse migration assay described above. To "invade", the cells need both (i) to move as in the transverse migration assay and (ii) secrete a proteolytic enzyme to digest their surroundings. The ability of cells to invade neighbouring tissues by enzyme secretion was therefore assessed by using a layer of Matrigel™ (BD Biosciences) spread across the porous membrane of a Transwell® insert. Matrigel™ is composed of laminin, collagen IV, nidogen/enactin and proteoglycan—a composition comparable to basement membrane proteins.

Figure 7:
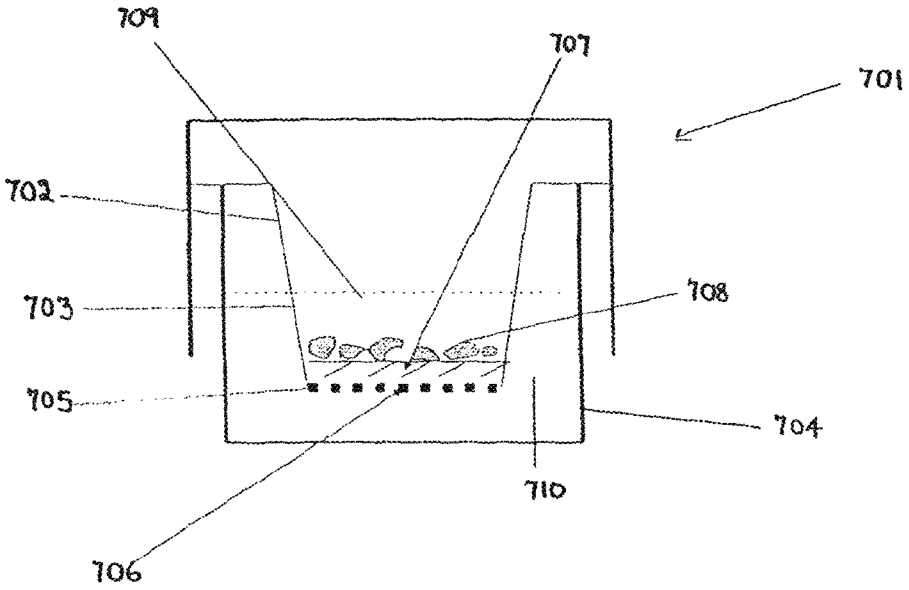
FIG. 7 is a schematic side sectional view of apparatus used for measuring the invasiveness of cells.

FIG. 7 is a schematic side sectional view of an invasion chamber 701 having a Transwell® insert 702 separating the chamber into upper 703 and lower 704 sections. The insert 702 has a migration filter membrane 705 in its base with 8 μm pores 706 extending therethrough. A layer 707 of Matrigel™ is shown coating the filter membrane 705.

Cells 708 were plated at a density of $2\times10^4$/ml onto the Matrigel™ layer 707 in 24-well plates (Becton-Dickinson) according to the manufacturers' instructions. 50 μl Matrigel™ was seeded at a 1:7 dilution (10 mg/ml stock) onto the inserts and left overnight. Prior to seeding with the cells the Matrigel™ was rehydrated using medium with no additions. This medium was removed prior to seeding the cells.

Cells were plated in a 1-5% FBS chemotactic gradient overnight (12 hours). The nutrient concentration in the medium 709 in the upper section 703 of the chamber was less than the concentration of nutrient in the medium 710 in the lower section 704 to induced movement of the cells through the Matrigel™ layer 707 and through the pores 706 to the underside of the filter membrane 705. At the end of each assay, non-invaded/non-migrated cells were removed from the upper surface of the insert 702 with two different swabs.

The number of cells invading to the underside of the insert 702 was determined using crystal violet staining. Invaded cells were fixed for 15 minutes with ice-cold methanol. Then 0.5 crystal violet (in 25% methanol) was added for 15 minutes. The inserts were swabbed again and then washed in water and allowed to dry. Cells were then counted using twelve separate fields of view per insert (×200 magnification). If the difference in the average number of cells invading the two control inserts was more than 40%, the experiment was rejected.

Cell Viability Assay

Cells were seeded at a density of $5\times10^4$ cells/ml in 35 mm Falcon tissue culture dishes. After treatment with a given drug, the medium was removed and replaced with 800 μl of growth medium and 200 μl 0.4% trypan blue (Sigma, Dorset, UK) and incubated for 10 minutes in the incubator. The trypan blue was removed and the cells were washed once with 3 ml growth medium. For each treatment, cells from 30 random fields of view were counted under 100× magnification. The number of dead cells, stained blue, was counted in each field of view. The data were expressed as percentages of living cells out of the total number of cells in given fields of view. The percentages were averaged and differences between control and treatment were compared from at least three independent experiments.

Cell Growth (Proliferation) Assay

Cells were plated at $2\times10^4$ cells/ml in 24-well plates (Becton-Dickinson) and allowed to settle overnight. The cells were then treated for the required time of incubation (24 hours+), with medium changes every 24 hours. At the end of the treatment, the medium was removed, and this was followed by the colorimetric 3-[4,5-dimethylthiazol-2-yl]-2,5-diphenyltetrazolium bromide (MU) assay (Grimes et al., 1995). Briefly, 0.1 ml MU (5 mg/ml made up in the growth medium) and 0.4 ml growth medium was added in each well and the plate was incubated for 3-4 hours at 37° C. The medium was then removed from the chambers and replaced with 0.5 ml dimethyl sulfoxide (DMSO) and 0.063 ml glycine buffer (0.1 M glycine and 0.1 M NaCl; pH 10.5). Absorbance at 570 nm was determined 15 minutes after the addition of the glycine buffer. Results were calculated as means of nine repeats of each of the treatment vs. control spectrophotometer readings from individual invasion wells.

Tissue Culture

Experiments were carried out on four strongly metastatic cell lines:

(i) human metastatic breast cancer MDA-MB-231, (ii) human metastatic colon cancer SW620 cells, (iii) human leukaemic FLG29.1 cells, and (iv) rat strongly metastatic prostate cancer Mat-LyLu.

Cells were cultured using known methods (e.g. Grimes et al., 1995; Fraser et al., 2005).

Normoxic and Hypoxic Conditions

With the exception of single cell adhesion tests, which are discussed in the following paragraph, experiments were carried out under either;

(i) normal normoxic conditions (95% oxygen, 5% carbon dioxide), or (ii) following 24 hours hypoxic pre-treatment (2% $O_2$, 5% $CO_2$, 93% $N_2$) continued during the assays.

In the single cell adhesion experiments, hypoxia was induced chemically by application of hydrogen peroxide (1-500 μM) for 24 hours.

EXAMPLES

Figure 8:
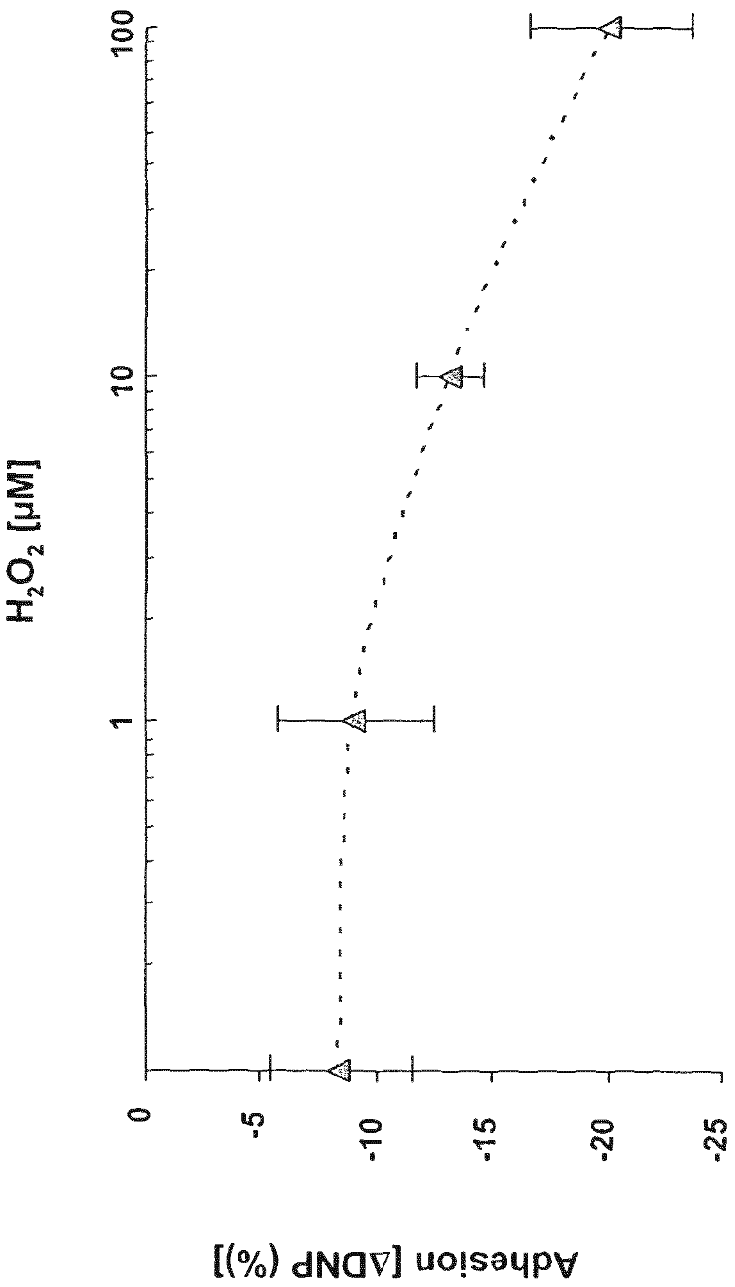
FIG. 8 is a graph showing the concentration dependent effect of chemically induced hypoxia on the single-cell adhesion of human metastatic breast cancer MDA-MB-231 cells. Adhesion increases ('detachment negative pressure'—DNP—decreases) under hypoxia.

Example 1—Effects of Chemical Hypoxia on the Single-Cell Adhesion of MDA-MB-231 Cells Chemical hypoxia was induced by treating cells with different concentrations of hydrogen peroxide for 24 hours. Single-cell adhesion was measured using the technique described above and illustrated in FIG. 4. The change in detachment negative pressure (ΔDNP) was expressed as a percentage versus a control population of untreated cells. Hypoxia reduced the cell adhesion and increasing the concentration of hydrogen peroxide, i.e., increasing the degree of hypoxia, led to greater reduction in cell adhesion as shown in FIG. 8. In this figure, the vertical axis represents the change in detachment negative pressure (ΔDNP), increasing downwardly so that a higher negative value is indicative of a cell's lower adhesion and, hence, its tendency to detachment. The horizontal axis is a logarithmic scale of hydrogen peroxide concentration, increasing from left to right.

Human breast cancer cells from the MDA-MB-23 1 cell line were plated in a cell culture dish at a density of $2.5\times10^4$ cells/ml and left to settle for 48 hours prior to measurements. The cells were subjected to hydrogen peroxide concentrations of 1 μM, 10 μM and 100 μM and the negative pressure required to detach cells from the bottom of the cell culture dish was measured. At each concentration of hydrogen peroxide, measurements were taken on at least two dishes of cells for at least 100 cells per dish. The experiment was repeated three times and the measurements of detachment negative pressure are presented in FIG. 8 as means±SEM.

In FIG. 8, it is shown that cells exposed to hydrogen peroxide at a concentration of 1 μM had a mean detachment negative pressure of approximately −9%, cells exposed to hydrogen peroxide at a concentration of 10 μM had a mean detachment negative pressure of approximately −14%, and cells exposed to hydrogen peroxide at a concentration of 100 μM had a mean detachment negative pressure of approximately −20%. Hence, increasing the concentration of hydrogen peroxide decreased the adhesion of the cells and made them easier to detach. In other words, increasing the severity of the hypoxic conditions led to an increase in the detachability of the cells.

Example 2—Effects of Eleclazine on a Highly Metastatic Breast Cancer Cell Line This Example describes the effects of eleclazine on cell viability, proliferation, motility, invasiveness, nNAV-1.5 expression, and transient and persistent sodium current, using the highly invasive human breast cancer cell line MDA-MB-231.

Material and Methods

Tissue Culture and Treatments:

MDA-MB-231 human breast cancer cells were seeded in 100×20 mm dishes (Thermo Fisher Scientific) using Dulbecco's Minimum Essential Medium (DMEM) with 4 mmol/L L-Glutamine and 5% fetal bovine serum (from now on referred to as media).

MDA-MB-231 cells naturally attach to tissue culture dishes due to their origin from human breast adenocarcinoma. 3 ml of 0.25% Trypsin-EDTA (Sigma Aldrich) was administered for 15 minutes to solubilise adherent cells, followed by centrifugation for 2 minutes at 1700 rpm. The pellet was re-suspended in media and the cell number was determined using a haemocytometer. Media was refreshed every 2-3 days and stock cells were kept in normoxic conditions at 37° C.

Eleclazine was dissolved in DMSO and stored as a concentration of 10 mM at −20° C. For the treatment of MDA-MB-231 cells, the drug was diluted in breast media to achieve concentrations of either 10 or 20 μM. The standard negative control was prepared by adding the same volume of 99.9% DMSO to media.

Cell Viability Assay:

Cell viability and therefore drug toxicity was determined using the trypan blue assay. The procedure follows the principle that viable cells surrounded by an intact double membrane cannot absorb the trypan blue dye, whereas dead and fragmented cells can. 35×10 mm dishes, initially containing $3\times10^4$ cells, were pre-treated with either 20 μM eleclazine or 0.4% DMSO for 48 hours.

The solution was subsequently replaced with 0.2 ml of 0.4% trypan blue (Sigma-Aldrich) and 0.8 ml of media. After 10 minutes, the trypan blue mixture was aspirated and replaced with media. Cell viability was determined by counting the proportion of viable and dead cells in 30 fields of view on each dish (Zeiss Axiovert 25 phase contrast microscope, ×40 magnification).

Proliferation Assay:

Proliferation was indirectly measured using MTT (3-(4, 5-dimethylthiazolyl-2)-2,5-diphenyltetrazolium). In principle, MTT is taken up and processed by metabolically active cells, which produce formazan as a by-product. Formazan is a purple dye which can be quantified on a spectrophotometer, providing a link between absorbance readings (570 nm) and cell number.

Cells were plated in 24-well plates at a density of $2\times10^4$ cells per well and pre-treated with 1 ml of the respective drug solutions (see FIG. 5.) for 48 hours in hypoxia and normoxia. 0.1 ml of MU (1 mg/ml) diluted in 0.4 ml of media was administered to each well, followed by 4 hours of incubation in dark, normoxic conditions (MU is light—sensitive). The solution was subsequently aspirated and 0.5 ml of 99.9% DMSO was added in combination with 75 μL glycine buffer. The dye was able to dissolve in DMSO during a 15 minute—incubation on a shaking platform at 150 cycles/minute. The absorbance was read using ELX800 Universal Microplate Reader (BioTek Instruments) with the background measuring 0.04. The data of three technical repeats (with 4 biological repeats each) was normalised and a statistical analysis was performed using SPSS.

Lateral Motility Assay:

$10^6$ cells were plated in each 35×10 mm dish and kept in normoxic conditions to settle overnight. Each dish was marked by 15 parallel vertical lines and 3 non-overlapping horizontal lines. The media was refreshed and three wounds were made along the marked vertical lines using a 1 ml Gilson pipette tip. Floating cells were removed by 3 consecutive media washes and adherent cells were treated with 1 ml of the respective drug solution (10 μM Eleclazine/DMSO). The initial wound width (W0) was measured at 45 fixed points (where the vertical lines cross the wounds) using the graticule on a phase-contrast microscope (×10 magnification). Cells were then incubated in both normoxic and hypoxic conditions, with drug solutions being replaced every 24 hours. Wound width was measured every 12 hours and the motility of this breast cancer cell line was analysed using the "motility index" (MI=1-(Wt/W0)). A motility index of 1 accounts for complete wound closure, whereas MI=0 represents zero cell movement. For each of the four conditions (Eleclazine and DMSO in normoxia and hypoxia), five technical repeats (including three biological repeats each) were performed. Data analysis was completed with SPSS Statistics.

Matrigel Invasion Assay:

Cells were pre-treated with 10 μM eleclazine or 0.2% DMSO for 24 hours under hypoxic conditions. Transwell filters with 8 μm pores were inserted into 24-well plates and coated with 62.6 μg Matrigel diluted in 50 μL FBS-free media. The matrigel solidified at 37° C. normoxia overnight and was hydrated at 37° C. normoxia for 3 hours using 0.5 ml FBS-free media. 300 μL of media containing 5% FBS was administered to the lower chamber and the same amount of media containing 1% FBS was added to the upper chamber (transwell filters). $2\times10^4$ cells were added to the 1% solution, allowing their invasion through the matrigel along the chemotactic gradient. Cells were left to settle and invade under hypoxic conditions overnight.

The following day, media in both chambers was aspirated and non-invaded cells were removed with a cotton swab. 100% ice-cold methanol was administered to the lower chamber to fix invaded cells, that were subsequently stained with 300 μL crystal violet (0.5 g/ml diluted in 25% methanol) for 15 minutes. The transwell filters were washed in distilled water and dried at room temperature for several hours.

Immunocytochemistry:

Cells were pre-treated with either 10 μM Eleclazine or DMSO in both normoxic and hypoxic conditions for 24 hours. The following day, round 13 mm coverslips were placed into 24-well plates and incubated with 0.5 ml poly-L-lysine for 20 minutes. The solution was aspirated and $2\times10^4$ pre-treated cells were added on top of each coverslip. The wells were filled up to 0.5 ml with the respective drug solutions and cells were left to settle onto the coverslips in normoxic and hypoxic conditions overnight.

Cells were washed with PBS and fixed by incubating coverslips with 0.5 ml 4% PFA (in PBS) for 15 minutes. Coverslips were then washed in PBS three times for 5 minutes. Half of the samples were permeabilised in 0.1% Saponin/PBS (4 minutes) followed by three 5 minute washes in PBS. Cells were blocked for 1 hour with 0.5 ml 5% BSA/PBS (pH 7.4). Coverslips were incubated with 70 μL NESOpAb (primary antibody specific for neonatal Nav1.5; 1:100 dilution) for 1 hour in a humidity chamber (room temperature). Three 5 minute PBS washes rinsed off residual NESOpAb and the secondary antibody (goat anti-rabbit IgG Alexa Fluor 568, 1:100 dilution) was administered for 1 hour in the dark. Three 5 minute washes were performed using PBS with 0.1% BSA and coverslips were mounted using Dako fluorescent mounting medium.

Imaging was conducted on a Zeiss axiovert 200 inverted microscope. Phase-contrast images were taken in jpeg format, fluorescent images were saved in raw format. The corrected total cell fluorescence was quantified using ImageJ.

Results

- 20 μM eleclazine had no effect on MDA-MB-231 cell viability.
- 10 μM eleclazine and 10 μM ranolazine did not influence cell proliferation during MTT assays.
- 10 μM eleclazine reduced lateral motility of highly metastatic breast cancer cells in hypoxic, but not normoxic conditions. This effect progressed from a 5% reduction after 12 hours to a 30% reduction after 48 hours.
- 5 μM eleclazine reduced invasiveness by approximately 50% and was more efficient than ranolazine.
- Immunocytochemistry indicated that 10 μM eleclazine reduced the expression of nNaV1.5 in both normoxic and hypoxic conditions. nNaV1.5 seemed to be higher expressed in normoxia compared to hypoxia.

Figure 9:
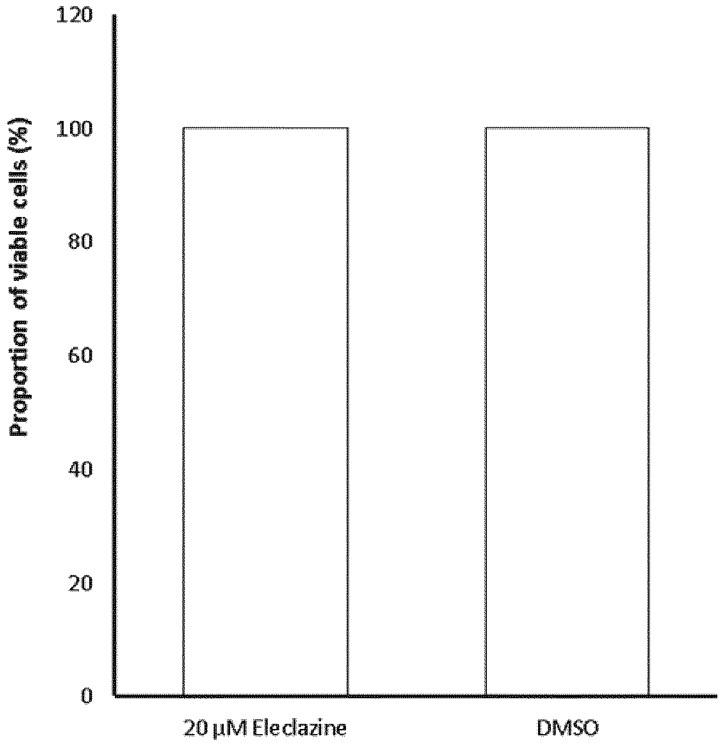
FIG. 9 is a graph showing the results of a Trypan Blue-cell exclusion (i.e. cell viability) assay. MDA-MB-231 cells were treated with 20 μM eleclazine or 0.2% DMSO (negative solvent control) for 48 hours. Cell viability was almost 100% for both treatment and control groups, showing that eleclazine was non-toxic.

Eleclazine was Non-Toxic to MDA-MB-231 Cells:

The analysis of 270 fields of view per treatment condition showed that 20 μM eleclazine did not have a significant effect on cell viability compared to 0.2% DMSO (FIG. 9). The average proportion of viable cells per field of view was 99.96% for both DMSO and eleclazine. The minimum proportion of viable cells was 93%. Considering these results and patch-clamp data (not shown), 10 μM was chosen as the concentration to proceed with (knowing that results are not confounded through cell death and that the persistent current is effectively blocked).

Figure 10A:
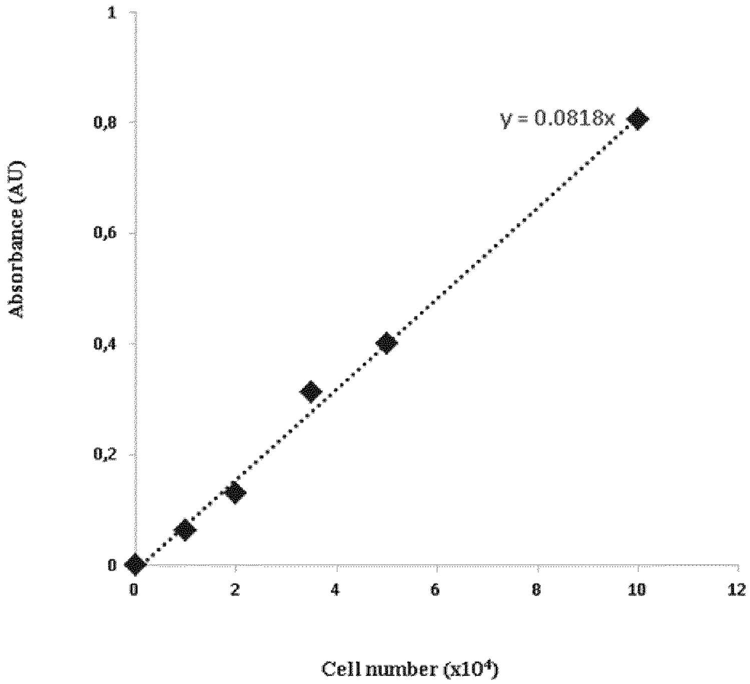
FIGS. 10A and 10B show the results of a MTT (Proliferation) Assay.

Neither Eleclazine, Nor Ranolazine Influenced Proliferation:

Because proliferation is an essential hallmark of cancer cells, it was of interest to determine whether eleclazine, as a potential anti-cancer drug, influences this process. The calibration curve presented in FIG. 10A shows that the number of cells plated in each well correlates linearly with the absorbance measured at 570 nm.

Figure 10B:
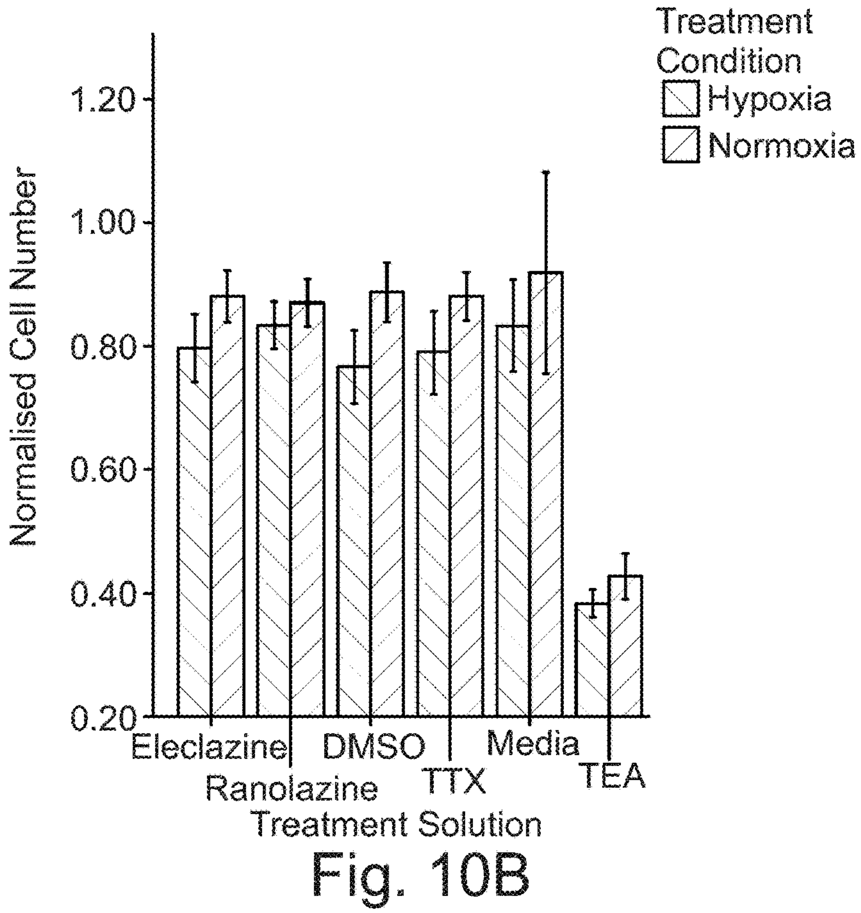

Data from the MTT assay was non-parametric and therefore analysed using a Mann-Whitney U test (95% confidence intervals). As presented in FIG. 10B, there was no statistically significant difference between 10 μM eleclazine and either of the negative controls (0.2% DMSO, 10 μM TTX, Media). Similarly, there was no significant effect of 10 μM ranolazine compared to the negative controls and eleclazine. 2 mM TEA (positive control) reduced cell proliferation by approximately 50%. For all treatments, hypoxia had a small dampening effect on cell proliferation. To conclude, eleclazine did not affect proliferation of triple negative breast cancer cells.

The Effect of Eleclazine on Lateral Motility:

A motility index (MI) was used to describe the rate at which MDA-MB-231 cells move in vitro. This rate was higher in hypoxia compared to normoxia. The difference between these two experimental conditions was statistically significant for all time points (95% confidence intervals) but the effect of hypoxia on motility did not increase over time.

Figure 11:
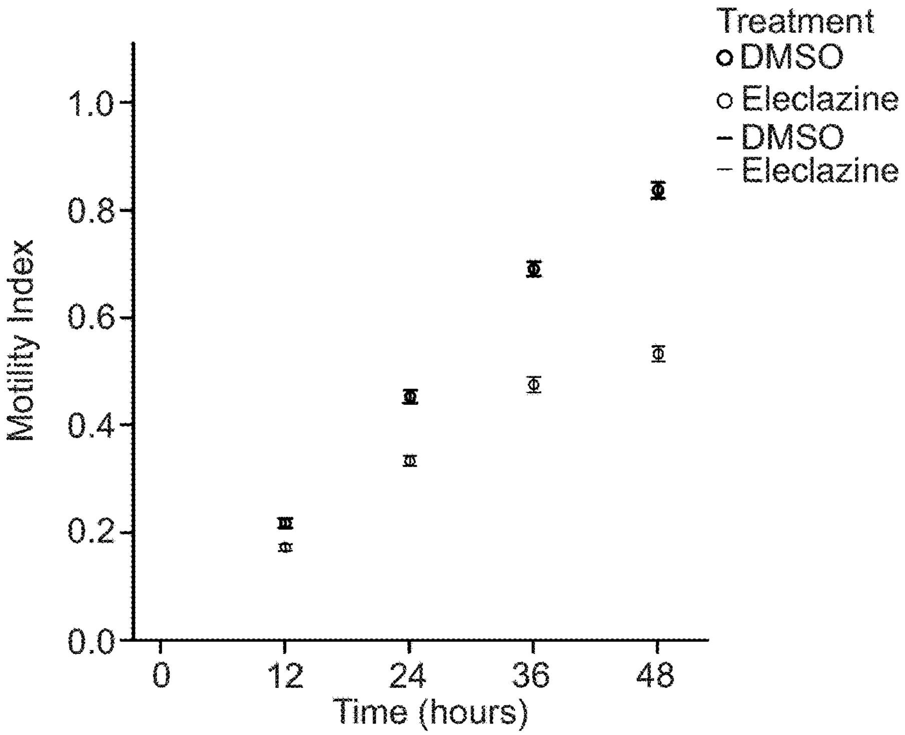
FIG. 11 shows the results of a wound heal assay. Motility index of hypoxic cells treated with either 0.2% DMSO or 10 μM Eleclazine for 48 hours. Eleclazine had a decreased lateral motility at all time points.

Eleclazine only reduced the rate of lateral motility during hypoxic, but not normoxic conditions (FIG. 11). This effect on cell motility increased over time. Starting off with an MI elevation of 5% after 12 hours, cells were 30% less motile after a 48-hour incubation with 10 μM eleclazine.

To conclude, 10 μM eleclazine effectively reduced the motility of MDA-MB-231 cells under hypoxic conditions.

Figure 12:
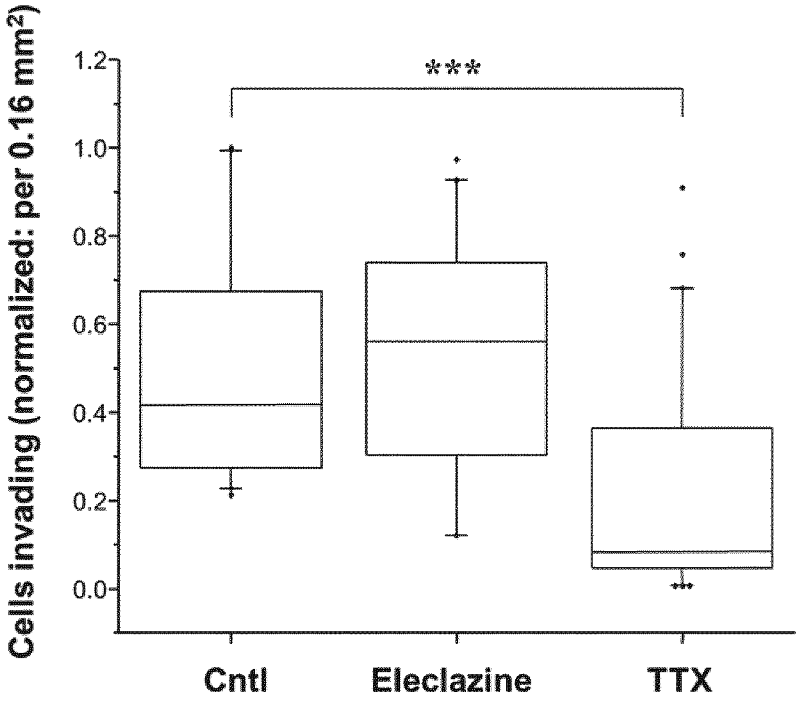
FIG. 12 shows the effect of 0.5 μM eleclazine and 20 μM tetrodotoxin (TTX) on invasion of MDA MB-231 cells under hypoxia (1% $O_2$) in vitro. The box plot indicates the normalized number of MDA MB-231 cells invading over 16 h following treatment with eleclazine or TTX in comparison to the control. Cells had been pre-incubated with the respective treatment conditions for 24 h before the start of the assay. 12 fields of view from 4 individual inserts were evaluated for each condition; *** indicates P<0.001). 0.5 μM eleclazine does not affect invasiveness; and 20 μM TTX decreases (positive control).
Figure 13:
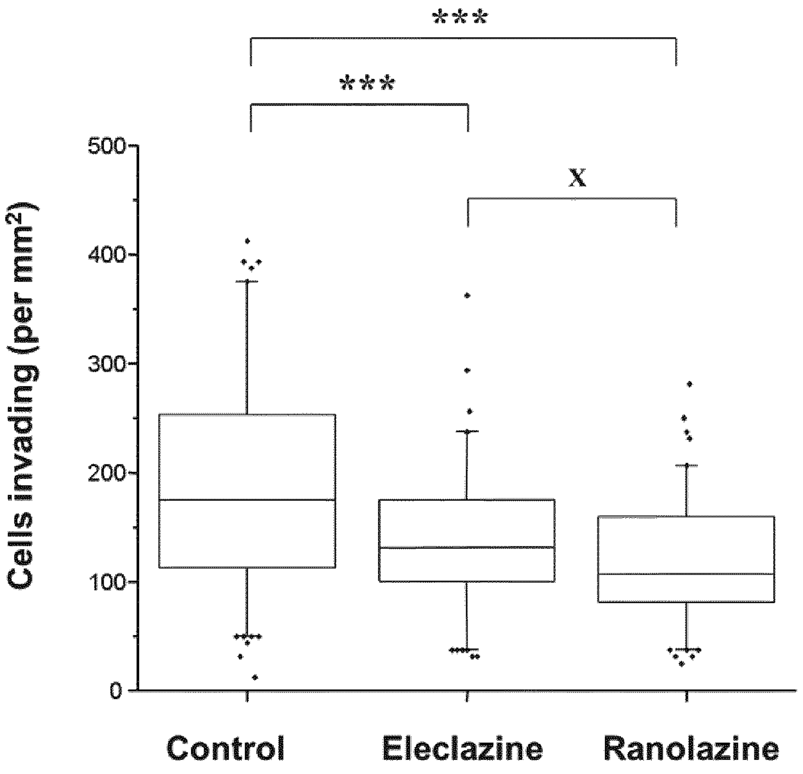
FIG. 13 shows the effect of 1 μM eleclazine and 1 μM ranolazine on invasion of MDA MB-231 cells under hypoxia (1% $O_2$) in vitro. The box plot indicates the number of MDA MB-231 cells invading over 16 h following treatment with eleclazine or ranolazine in comparison to the control. Cells had been pre-incubated with the respective treatment conditions for 24 h before the start of the assay. Median values and interquartile range were as follows: Control: 175.0 (113 & 255); 1 μM eleclazine 131.5 (100 & 175) and 1 μM ranolazine 106.3 (181 & 161). 12 fields of view from 8 individual inserts for each condition; *** indicates P<0.001; X indicates P>0.05. Eleclazine and ranolazine (both 1 μM) suppress invasiveness significantly but similarly.
Figure 14:
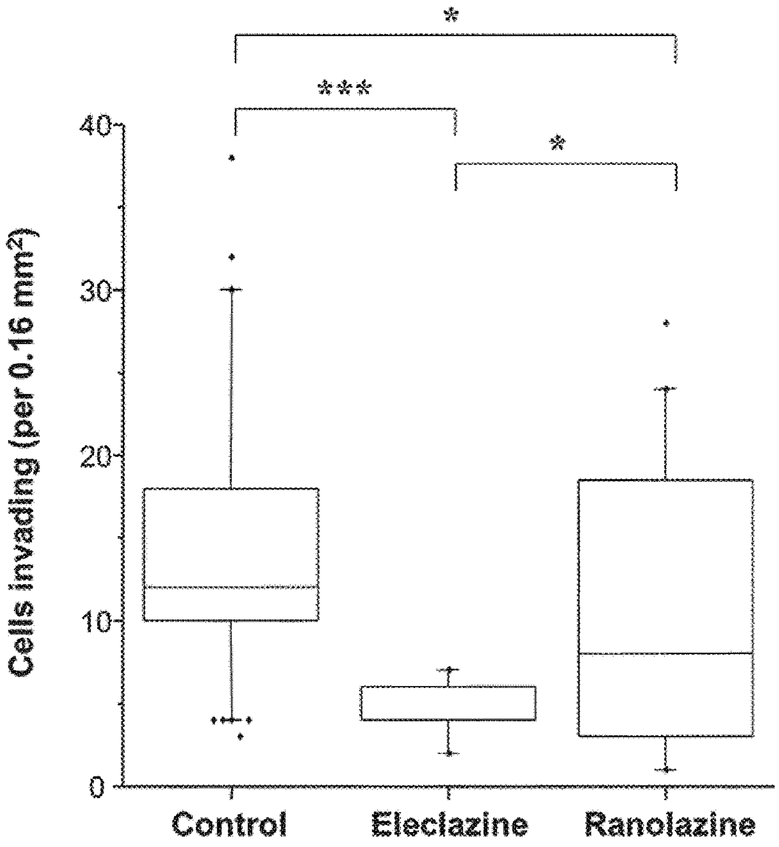
FIG. 14 shows the effect of 5 μM eleclazine and 5 μM ranolazine on invasion of MDA MB-231 cells under hypoxia (1% $O_2$) in vitro. The box plot indicates the number of MDA MB-231 cells invading over 16 h following treatment with eleclazine or ranolazine in comparison to the control. Cells had been pre-incubated with the respective treatment conditions for 24 h before the start of the assay. 12 fields of view from 8 individual inserts for each condition; *** indicates P<0.001; X indicates P>0.05. Eleclazine and ranolazine (both 5 μM) suppress invasiveness significantly but the effect of eleclazine was significantly greater.

The Effect of Eleclazine on Invasiveness:

Invasiveness was quantified as the number of cells per field of view that migrated through the matrigel. Preliminary assays had shown that 10 μM eleclazine drastically reduced the invasiveness of MDA-MB-231 cells in hypoxic conditions. The following experiments therefore examined the effect of lower concentrations. See FIG. 12 for results with 0.5 μM eleclazine and 20 μM tetrodotoxin (TTX) on invasion of MDA MB-231 cells under hypoxia. Both eleclazine and Ranolazine reduced invasiveness at concentrations as low as 1 μM, but there was no statistically significant difference between the two VGSC blockers (FIG. 13). As presented in FIG. 14, 5 μM eleclazine reduced invasiveness of MDA-MB-231 cells by approximately 50% and was significantly more effective than 5 μM Ranolazine.

Figure 15:
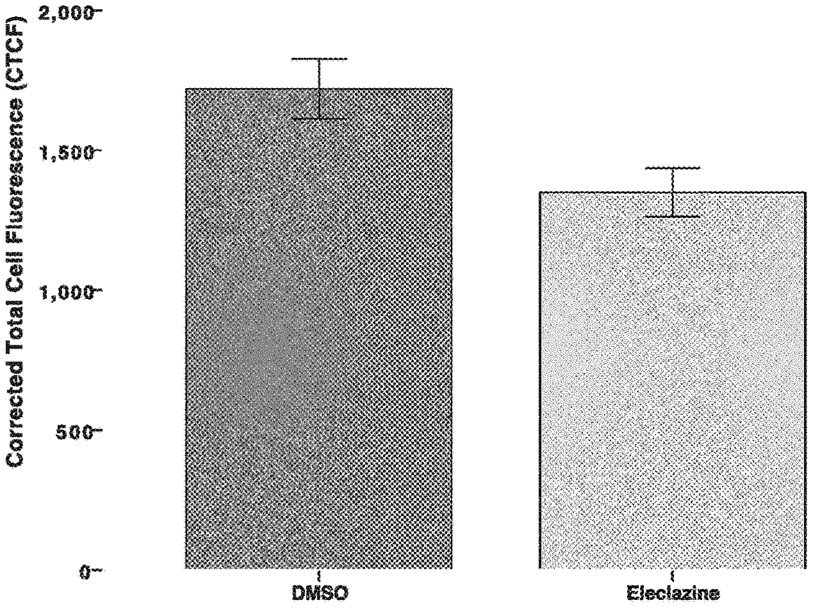
FIG. 15 shows the effect of eleclazine (10 μM) on the corrected total cell fluorescence of MDA-MB-231 cells stained for nNav1.5 protein expression. Eleclazine treatment decreases the expression.

Eleclazine Reduced nNav1.5 Protein Expression:

The influence of eleclazine on the expression of neonatal NaV1.5 protein expression in MDA-MB-231 cells was quantified using immunocytochemistry—parameter: corrected total cell fluorescence (CTCF). As visualized in FIG. 15, 24 hour treatment with 10 μM eleclazine caused a statistically significant reduction. This indicates that eleclazine blocks both activity and expression of nNav1.5.

Example 3—Effect of Eleclazine on Invasiveness of a Human Leukaemic Cell Line This Example describes the anti-invasive effects of eleclazine and ranolazine on a human leukaemic cell line (FLG29.1). FLG 29.1 cells were cultured in RPMI medium supplemented with 10% fetal calf serum and incubated at 37° C. in 5% $CO_2$. For hypoxia, cells were pre-exposed to 1% oxygen for 24 h. In invasion assays, cells were plated on Matrigel (diluted 1:7) and treated (no pre-treatment) with eleclazine, ranolazine (5 μM each) or TTX (0.1 or 10 μM). Cells were allowed to invade through transwell filters with 8 μm pores for 18 h. The following day, media in both chambers was aspirated and non-invaded cells were removed with a cotton swab. 100% ice-cold methanol was administered to the lower chamber to fix invaded cells that were subsequently stained with 300 μL crystal violet (0.5 g/ml diluted in 25% methanol) for 15 minutes. The transwell filters were washed in distilled water and dried at room temperature for several hours. Invaded cells were counted under a microscope in randomly chosen fields of view. Data were expressed as percentage of cells that invade.

Figure 16:
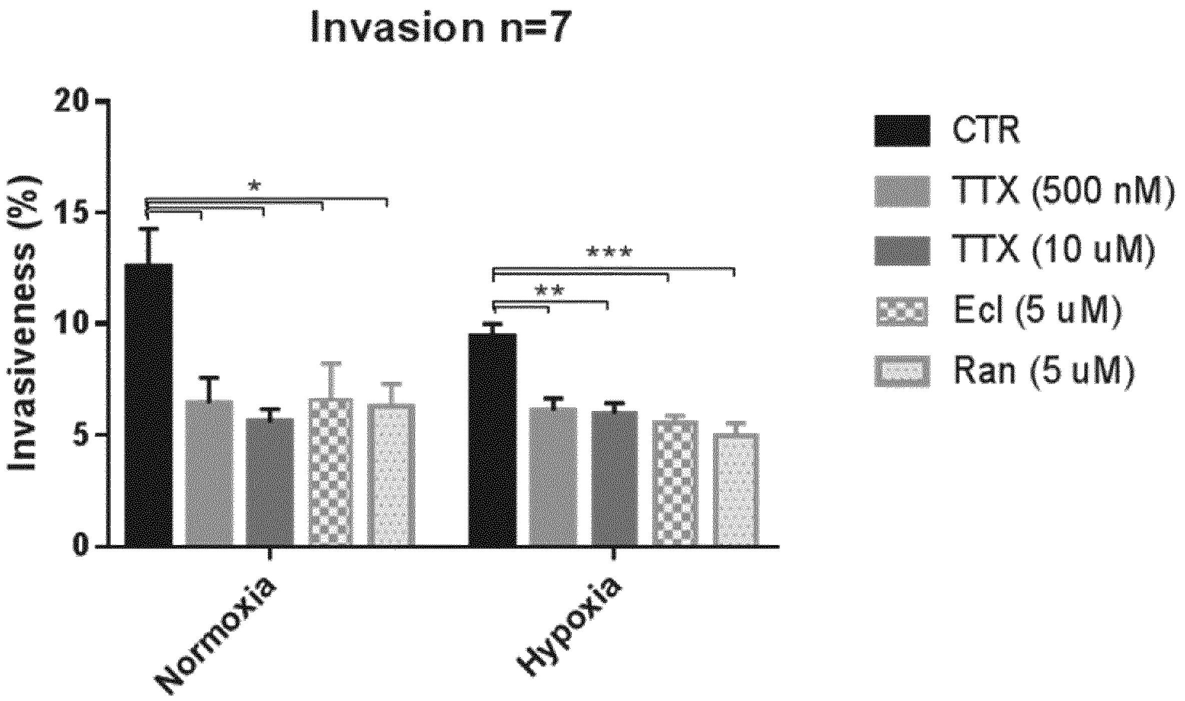
FIG. 16 shows the effects of eleclazine, ranolazine (both 5 μM) and TTX (0.1 and 10 μM) on invasiveness of human leukaemic FLG 29.1 cell line under normoxia and hypoxia (1% $O_2$). All agents (TTX used as positive control) significantly inhibited invasiveness.

All agents (TTX used as positive control) significantly inhibited invasiveness, as shown in FIG. 16.

LIST OF REFERENCES

Fraser S P, et al. (2005). Voltage-gated sodium channel expression and potentiation of human breast cancer metastasis. Clin Cancer Res. 11: 5381-5389.

Grimes J A, et al. (1995). Differential expression of voltage-activated Na+ currents in two prostatic tumour cell lines: contribution to invasiveness in vitro. FEBS Letters 369: 290-294.

Palmer C P, et al. (2008). Single cell adhesion measuring apparatus (SCAMA): application to cancer cell lines of different metastatic potential and voltage-gated Na+ channel expression. Eur Biophys J. 37: 359-368.

Puller H, et al. (2016). Eleclazine, a new selective cardiac late sodium current inhibitor, confers concurrent protection against autonomically induced atrial premature beats, repolarization altemans and heterogeneity, and atrial fibrillation in an intact porcine model. Heart Rhythm 13(8): 1679-1686.

Martin F., et al. (2015). Therapeutic Value of Voltage-Gated Sodium Channel Inhibitors in Breast, Colorectal, and Prostate Cancer: A systematic Review. Frontiers in Pharmacology, Vol. 6, Article 273: 1-11.

Moss A J, et al. (2008). Ranolazine Shortens Repolarization in Patients with Sustained Inward Sodium Current Due to Type-3 Long-Q T Syndrome. J Cardiovasc Electrophysiol 19(12): 1289-1293.

Djamgoz M, et al. (2011). Bioelectricty of Cancer: Voltage-Gated Ion Channels and Direct-Current Electric Fields. Page 267 et seq. In: The Physiology of Bioelectricity in Development, Tissue Regeneration and Cancer (Ed: Pullar C E). CRC Press, Boca Raton, Fla.

Roger S, et al. (2015). Voltage-gated sodium channels and cancer: is excitability their primary role? Front Pharmacol; 6: 152.

Fuller H, et al. (2016). Eleclazine, a new selective cardiac late sodium current inhibitor, confers concurrent protection against autonomically induced atrial premature beats, repolarization alternans and heterogeneity, and atrial fibrillation in an intact porcine model. Heart Rhythm 13(8):1679-86.

Brackenbury W3 (2012). Voltage-gated sodium channels and metastatic disease. Channels (Austin) 6(5):352-61.

Diss J K, et al. (2001). Expression profiles of voltage-gated Na(+) channel alpha-subunit genes in rat and human prostate cancer cell lines. Prostate 48(3):165-78.

Trendowski M (2015). The inherent metastasis of leukaemia and its exploitation by sonodynamic therapy. Crit Rev Oncol Hematol 94(2):149-63.

Rajamani S, et al. (2016). The novel late Na+ current inhibitor, GS-6615 (eleclazine) and its anti-arrhythmic effects in rabbit isolated heart preparations. Br J Pharmacol. 173(21):3088-3098.

US 2015/0283149 A1 (Belardinelli L, et al.)

US 2012/0245144 A1 (Heffron T, et al.)

WO 2012/049440 A1 (Imperial Innovations Limited)

WO 2012/049439 A1 (Imperial Innovations Limited)

WO 2015/017661 A1 (Gilead Sciences, Inc.)

US 2017/0007617 A1 (Strickley R)

ClinicalTrials.gov identifier NCT02291237

ClinicalTrials.gov identifier NCT02104583

The invention claimed is:

1. A method for inhibiting the metastatic and invasive growth of malignant cells in a cancer patient suffering from an Nav1.5 expressing cancer, comprising administering to the patient a therapeutically effective amount of a compound of the formula I,

I

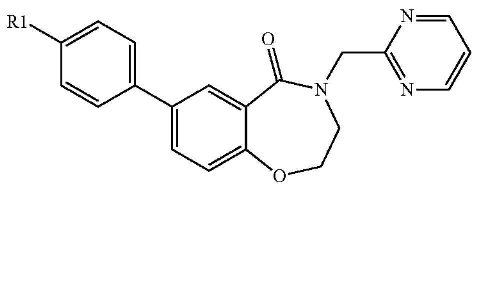

wherein R1 is trifluoromethyl or trifluoromethoxy, or a pharmaceutically acceptable salt thereof, wherein the therapeutically effective amount reduces the persistent part of the Nav1.5 current without eliminating the transient part of the current.

2. The method according to claim 1, wherein the cancer cell expression of Nav1.5 is decreased.

3. The method according to claim 2, wherein the cancer cell expression of neonatal Nav1.5 is decreased under hypoxic conditions.

4. The method according to claim 1, wherein R1 is trifluoromethoxy and the compound is of the formula Ia

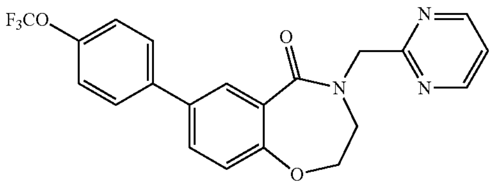

5. The method according to claim 1, wherein R1 is trifluoromethyl and the compound is of the formula Ib

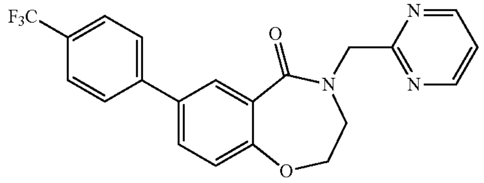

6. The method according to claim 1, wherein the cancer expresses neonatal Nav1.5.

7. The method according to claim 1, wherein the cancer is a haematological cancer or a solid tumour cancer.

8. The method according to claim 7, wherein the cancer is a leukaemia, a lymphoma, a carcinoma, a mesothelioma, a sarcoma, a melanoma, or a neuroblastoma.

9. The method according to claim 7, wherein the cancer is breast cancer, colon cancer, prostate cancer, non-small cell lung carcinoma (NSCLC), pleural cancer, cervical cancer, ovarian cancer, gastric cancer, or neuroblastoma.

10. The method according to claim 1, wherein the method inhibits the metastatic and invasive growth of malignant cells in Nav1.5 expressing cancer without killing the cancer cells.

11. The method according to claim 1, wherein the metastatic and invasive growth of malignant cells is inhibited by:

(a) reducing the invasiveness of cancer cells;

(b) reducing the motility of cancer cells, optionally under hypoxic conditions;

(c) reducing the ability of cancer cells to migrate; or (d) a combination of (a) and (b), (b) and (c), (a) and (c), or (a) to (c).

12. The method according to claim 1, wherein the compound is administered at a dosage level corresponding to the range 1 μmol to 10 μmol.

13. The method according to claim 1, wherein the compound is administered at a dosage from about 1 mg to about 30 mg.

14. The method according to claim 13, wherein the compound is administered at a dosage of about 3 mg, about 5 mg, about 6 mg, about 9 mg, about 10 mg, about 12 mg, about 15 mg, or about 19 mg.

15. A method for inhibiting the metastatic and invasive growth of malignant cells in a cancer patient suffering from a neonatal Nav1.5 expressing cancer, comprising administering to the patient a therapeutically effective amount of a compound of the formula Ia, Ia

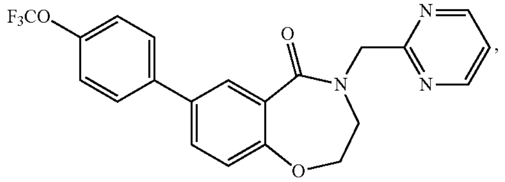

or a pharmaceutically acceptable salt thereof, wherein the therapeutically effective amount decreases the expression of neonatal Nav1.5.

16. The method according to claim 15, wherein the expression of neonatal Nav1.5 is determined by an immunohistochemical analysis of a cancer cell-containing sample from the patient.

17. The method according to claim 15, wherein the cancer is breast cancer, colon cancer, prostate cancer, non-small cell lung carcinoma (NSCLC), pleural cancer, cervical cancer, ovarian cancer, gastric cancer, or neuroblastoma.

18. The method according to claim 15, wherein the method inhibits the metastatic and invasive growth of malignant cells in neonatal Nav1.5 expressing cancer without killing the cancer cells.

19. The method according to claim 15, wherein the compound is administered at a dosage level corresponding to the range 1 μmol to 10 μmol.

20. The method according to claim 15, wherein the therapeutically effective amount decreases the expression of neonatal Nav1.5 under hypoxic conditions.

21. A method of decreasing the expression of neonatal Nav1.5 on Nav1.5 expressing cancer cells in a patient suffering from a Nav1.5 expressing cancer, comprising administering to the patient a therapeutically effective amount of a compound of the formula Ia, Ia

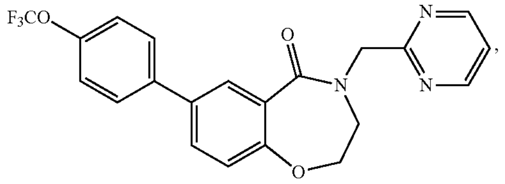

or a pharmaceutically acceptable salt thereof, thereby inhibiting the metastatic and invasive growth of malignant cells of the Nav1.5 expressing cancer in the patient.

* * * * *